(12) United States Patent
Schiewe et al.

(10) Patent No.: US 7,699,052 B2
(45) Date of Patent: Apr. 20, 2010

(54) APPARATUS FOR THE DISPENSING OF LIQUIDS, CONTAINER CARTRIDGE SUITABLE FOR THIS, AND SYSTEM COMPRISING THE APPARATUS FOR THE DISPENSING OF LIQUIDS, AND THE CONTAINER CARTRIDGE

(75) Inventors: Joerg Schiewe, Mainz (DE); Gilbert Wuttke, Dortmund (DE); Bernd Zierenberg, Bingen (DE); Stephen Dunne, Great Finborough/Stowmarket (GB); Horst Wergen, Wuppertal (DE)

(73) Assignee: Boehringer Ingelheim Pharma GmbH & Co. KG, Ingelheim am Rhein (DE)

( * ) Notice: Subject to any disclaimer, the term of this patent is extended or adjusted under 35 U.S.C. 154(b) by 903 days.

(21) Appl. No.: 10/648,132

(22) Filed: Aug. 26, 2003

(65) Prior Publication Data
US 2004/0094146 A1  May 20, 2004

Related U.S. Application Data

(60) Provisional application No. 60/430,564, filed on Dec. 3, 2002.

(30) Foreign Application Priority Data
Sep. 5, 2002 (DE) ............................. 102 41 640
Dec. 3, 2002 (EP) ............................. 02027030

(51) Int. Cl.
*A61M 11/00* (2006.01)
*A61M 5/30* (2006.01)
*A61M 5/20* (2006.01)
*A61M 5/315* (2006.01)
*B05B 9/04* (2006.01)

(52) U.S. Cl. ........................... 128/200.22; 128/200.14; 239/321; 239/322; 604/68; 604/135; 604/218

(58) Field of Classification Search ............ 128/200.11, 128/200.12, 200.14, 200.17, 200.18, 200.21, 128/200.22, 200.23, 200.24, 202.17, 203.15; 222/402.2, 182, 183, 82, 83, 83.5, 326, 327, 222/321.6, 386; 239/320–323; 604/68–70, 604/35, 218, 208, 143, 135
See application file for complete search history.

(56) References Cited

U.S. PATENT DOCUMENTS 4,561,856 A * 12/1985 Cochran .................... 604/143

(Continued)

FOREIGN PATENT DOCUMENTS

DE    10216101.1    6/1998

(Continued)

OTHER PUBLICATIONS

Copy of International Search Report Reference #PCT/EP 03/09442.

*Primary Examiner*—Steven O Douglas
*Assistant Examiner*—Annette F Dixon
(74) *Attorney, Agent, or Firm*—Michael P. Morris; Mary-Ellen M. Devlin; Alan R. Stempel

(57) ABSTRACT

The present invention relates to a propellant-gas-free apparatus for the dispensing of liquids, a container cartridge suitable for this for storing the liquid and the ensemble comprising both. The invention comprises a device for the exertion of pressure and for accommodating a container cartridge and a container cartridge in which the dispensing facility is integrated.

16 Claims, 18 Drawing Sheets

U.S. PATENT DOCUMENTS

| | | | |
|---|---|---|---|
| 4,623,337 A | | 11/1986 | Maurice |
| 5,121,464 A * | | 6/1992 | Hanada et al. ............... 392/405 |
| 5,964,416 A * | | 10/1999 | Jaeger et al. ................. 239/333 |
| 6,401,987 B1 | | 6/2002 | Oechsel et al. |
| 6,550,477 B1 * | | 4/2003 | Casper et al. .......... 128/203.21 |
| 6,595,205 B2 * | | 7/2003 | Andersson et al. ..... 128/200.23 |
| 6,644,309 B2 * | | 11/2003 | Casper et al. .......... 128/203.21 |
| 6,708,846 B1 * | | 3/2004 | Fuchs et al. .................... 222/82 |
| 2003/0070679 A1 * | | 4/2003 | Hochrainer et al. .... 128/203.15 |
| 2007/0119968 A1 * | | 5/2007 | Collins et al. ............ 239/102.1 |
| 2007/0119969 A1 * | | 5/2007 | Collins et al. ............ 239/102.1 |

FOREIGN PATENT DOCUMENTS

| | | |
|---|---|---|
| EP | 0860210 | 8/1998 |
| EP | 0918570 | 6/1999 |
| EP | 1100474 | 5/2001 |
| WO | 9407607 | 4/1994 |
| WO | 9712683 | 4/1997 |
| WO | 9916530 | 4/1997 |
| WO | WO 97/12687 | 4/1997 |
| WO | 9720590 | 6/1997 |
| WO | 9806502 | 2/1998 |
| WO | 0007572 | 2/2000 |
| WO | WO 00/47332 | 8/2000 |
| WO | 9114468 | 3/2001 |
| WO | 0164268 | 9/2001 |

* cited by examiner

APPARATUS FOR THE DISPENSING OF LIQUIDS, CONTAINER CARTRIDGE SUITABLE FOR THIS, AND SYSTEM COMPRISING THE APPARATUS FOR THE DISPENSING OF LIQUIDS, AND THE CONTAINER CARTRIDGE

CROSS-REFERENCE TO RELATED APPLICATIONS

Benefit of U.S. Provisional Application Ser. No. 60/430,564, filed on Dec. 3, 2002 is hereby claimed.

BACKGROUND OF THE INVENTION

1. Field of the Invention

The present invention relates to a propellant-gas-free apparatus for the dispensing of liquids, a container cartridge suitable for this for storing the liquid and the ensemble comprising both.

2. Description of the Related Art

The international patent application WO 91/14468 "Atomizing Device and Methods" or also WO 97/12687 disclose a device for the propellant-gas-free administration of a dosed quantity of a liquid drug for inhalative application. Reference is hereby made expressly to the said references and the technology described there is called "Respimat® technology" within the framework of the present invention. This term also includes in particular the technology on which a device according to FIGS. 6a and 6b of WO 97/12687 and the associated description is based in principle, in particular the technology for the exertion of pressure, the locking clamping means and the means for the dispensing of the liquid (nozzle). These inhalers can already atomize quantities of less than 100 microlitres of a liquid active ingredient solution in the therapeutically necessary dosage with preferably a single stroke into a therapeutically-inhalatively suitable aerosol within a few seconds. This consists of particles of an average size of less than 20 micrometres. The inhalable portion of the aerosol corresponds to the therapeutically effective quantity.

In these nebulizers based on Respimat® technology a drug solution is converted by means of high pressure of up to 500/600 bar into a lung-accessible aerosol and sprayed. The solution formulations are stored in a reservoir. From there they are conveyed via a riser tube into a pressure chamber and further nebulized via a nozzle. It is necessary that the active ingredient formulations used display an adequate storage stability and at the same time their state is such that they can be applied directly if at all possible without further manipulation according to the medicinal purpose. Furthermore, they must not contain constituents which can interact with the inhaler so that the inhaler or the pharmaceutical quality of the solution, respectively of the produced aerosol, could be damaged.

WO 01/64268 describes a further device of this type: a needleless injector which operates with a pressure-exertion means similar to the device of WO 97/12687.

A further device which is not based on the previously named technology is described in EP 0918570. Here an atomizer for nose sprays is disclosed which contains, as core elements, a spring-operated piston and a nozzle facility. Between piston and nozzle a container can be inserted which has a plunger on the bottom side and is closed top-side via a seal. This seal of the container is opened before first use by moving the nozzle, integrated in the atomizer, by pushing the nozzle through the seal.

The described devices from the state of the art are intended primarily for continuous use, i.e. for a use without lengthy breaks. In the case of a lengthy time break the part of the solvent of the liquid active ingredient formulation that is located outside the reservoir in only small volumes in the pumping- and/or pressure- and/or spray mechanism can evaporate and lead there to a formulation with a concentrated quantity of active ingredient or the formulation dries up. In these cases the device must, prior to re-use, first be cleaned again by single or multiple activation and spraying of the active ingredient formulation into the air.

SUMMARY OF THE INVENTION

The present invention relates to a device which, building on the Respimat® technology, has the object of providing a discontinuous, i.e. occasional administration of a liquid drug formulation with reproducible dosing accuracy.

A further object is to be able in such cases to dispense with cleaning steps between the discontinuous applications.

A further object is to provide a nebulizer for the discontinuous administration of liquid active ingredient formulations in which a drying-up of liquid in the system that threatens the pharmaceutical quality of the formulation or the pharmaceutical quality of the application is largely minimized.

A further object is to provide such a device in which the use of preservatives in active ingredient formulations can optionally be dispensed with.

A further object is to provide such a device with which liquid active ingredient formulations can also be nebulized which under normal conditions (i.e. under air or oxygen atmosphere) or during non-sterile treatment quickly suffer loss of pharmaceutical quality.

Finally it is an object of the present invention to make available a device for the delivery of a dosed quantity of a liquid drug formulation as a liquid jet or as an aerosol of droplets by delivery of a dosed quantity of the drug under pressure by dispensing facility which does not display the aforementioned disadvantages of the known devices.

A further object of the invention is to provide a nebulizer for the preparation of an inhalable aerosol.

A further object of the invention is to provide a needleless injector for the preparation of a jet injecting itself in or through the skin of an animal/human or a human, animal or vegetable membrane.

A further object of the invention is to provide an atomizer for the application of an aerosol to the surface of the eye.

A further object of the invention is to provide a device for the dispensing of pharmaceutical liquids for needleless injection, inhalation, nebulizing etc. which satisfies the high hygiene requirements of a medical device.

In particular the invention comprises: a device for the exertion of pressure on a reservoir (container cartridge), which has means for accommodating the reservoir; and the reservoir itself, whereby a dispensing facility for liquid, e.g. in the form of a nozzle and/or nozzle facility, is integrated into this.

The apparatus according to the invention can be used e.g. as a needleless injector or as an atomizer. As an atomizer it serves to provide an aerosol of droplets for inhalative intake through the mouth and throat area into the lung of a patient or for nasal intake. The atomizer according to the invention can also be used for eye treatment with the help of a supplementary adapter.

Within the framework of the present description of the invention, the term apparatus is equated with the terms device, needleless injector, atomizer or else dosing inhalation device. The terms can be used alongside each other as equivalents. Depending on the context, either only the device for the exertion of pressure or the ensemble of same together with the container cartridge can be meant by these terms. The difference between the atomizer according to the invention and the needleless injector consists in functional terms mainly in the configuration of the dispensing facility: in the case of the needless injector this is so designed that a liquid jet emerges from it which remains as such. In the case of the atomizer the dispensing facility is so designed that either an aerosol emerges from it and/or at least two liquid jets meeting each other, which are atomized into an aerosol by the reciprocal impact. The nebulizer according to the invention preferably serves as an inhaler for liquid pharmaceutical active ingredient formulations. The latter are preferably propellant-gas-free and the pharmacologically active constituents are preferably dissolved or suspended in water, in water-ethanol mixtures or in other pharmacologically compatible, non-volatile liquids. The formulations are preferably solutions based on water and/or water-ethanol.

Such formulations lead in the case of inhalative application to an optimal active ingredient distribution of the active substances in the lung when they are converted, by mean of inhalers suitable for this, into lung-accessible aerosols.

BRIEF DESCRIPTION OF THE FIGURES

The invention will be described in more detail in the following with reference to embodiments.

FIG. 4 shows a version with housing middle section 2b and housing lower section 3 swivellable vis-à-vis the housing upper section 2a.

DETAILED DESCRIPTION OF THE INVENTION

Figure 1:
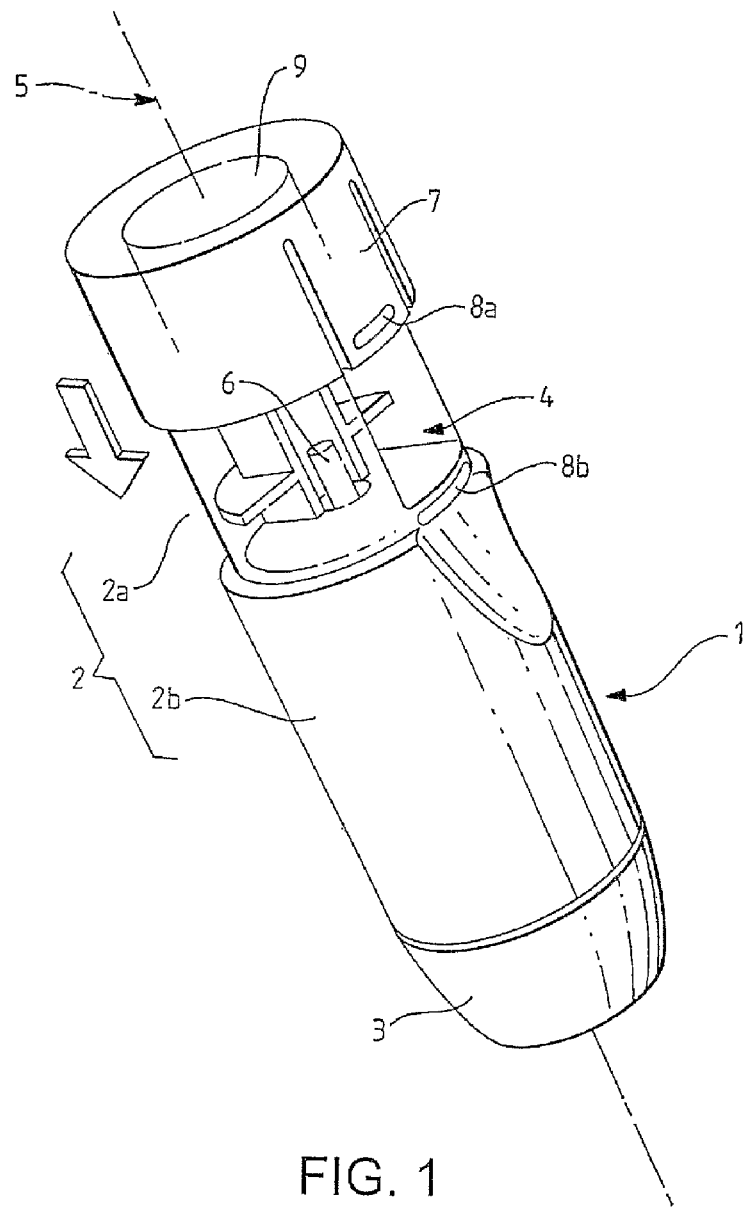
FIG. 1 shows a cylinder-symmetrical version of the device according to the invention.

Contrary to the known devices which are designed as multi-dose devices such that as a rule a device contains all the technology provided for the dispensing of the liquid and this device is fitted with a drug container which contains so much drug that up to several hundred single doses can be administered to the patient, the invention is based on a completely different inventive concept.

According to the invention a device is provided in which the technology needed for the dispensing of the liquid is broken down into two part-aspects: according to the invention the technology necessary for the dispensing of the liquid and the components necessary for this is divided into at least two structurally separate parts. On the one hand a part (primary packing means) which provides the elements necessary for supplying the drug and the elements coming into direct contact with the drug. On the other hand a second part which contains the elements which provide the energy and the mechanics for the dispensing process.

Accordingly, on the one hand a device for the dispensing of a liquid is thus created, and on the other hand a reservoir for accommodating the liquid with a dispensing facility integrated with it or firmly connected to this container as an integral constituent. This container is preferably created as a container cartridge which is fitted into the device for the dispensing of the liquid.

The device for the dispensing of the liquid contains: means for the respective introduction and removal of the container cartridge containing the drug into and from the inside of the device; and means for the exertion of pressure on the container cartridge.

Within the framework of the present invention this device is also called device for pressure exertion or device.

This device is re-usable, i.e. it is designed for a large number of single activations and serves essentially to accommodate the container cartridge together with dispensing facility and to dispense the liquid in the container via the dispensing facility of the container. For this, the device makes available a mechanism for the exertion of pressure on the container or the liquid in its inside.

The container cartridge according to the invention itself contains, in addition to the integrated dispensing facility, means which pass the pressure created by the device onto the liquid in the inside of the container, in order to feed the thus-pressurized liquid to the dispensing facility.

The container is also called reservoir, container cartridge or just cartridge within the framework of this description of the invention.

The container cartridge contains the drug and thus serves as primary packing means. Additionally, the container contains all the elements which directly come into contact with the drug. These include in particular the actual dispensing facility which is preferably a nozzle. The container can for example be developed as a disposable container, e.g. as a single-use container.

As already stated, the liquid is preferably a pharmaceutical formulation, e.g. drug solutions or drug suspensions.

The objects on which the invention is based are achieved by the provision according to the invention of a pressure-creating device and a primary packing means independent of this for the drug preparation. Since with every application a new container cartridge can be used in the device for the provision of the pressure exertion, this guarantees for example that, even if the device is not used over a lengthy period, the drug formulation is not impaired as the cartridge remains unused.

The fact that the container cartridges can be such that they accommodate only a single dose unit, i.e. only a single application is possible or the quantity and drug is sufficient for only a few doses, allows preservative-free drugs to be used. This not only results in the patient being burdened with a small quantity of antimicrobially active substances, but also makes possible drug formulations of drugs (such as e.g. peptides) which cannot be formulated in a stable manner together with preservatives approved for inhalation. The freedom from preservatives that can be realized with the device according to the invention therefore allows drugs, that were previously unable to be formulated because of incompatibility with preservatives, to actually be made available.

FIG. 1 shows a device 1 according to the invention in a cylinder-symmetrical version. It consists of a housing upper section 2a, the housing middle section 2b, which are also both together numbered 2 as a structural unit, and housing lower section 3. The upper housing section 2 is covered by a protective cap 7. The device 1 has an opening 4 through which a view into the inside is made possible. There is located at the centre of the axis of symmetry 5 a mobile element in the form of a pressure piston 6 above which in direct manner the container cartridge 10 (cf. FIG. 2) lies. Through succeeding movement of the protective cap 7 parallel to the axis of symmetry 5 in the direction of the arrow, the device 1 is closed and is ready for use, in which e.g. an aerosol emerges in droplet form from the opening 9. In order to prevent an inadvertent opening, a locking mechanism 8a, 8b is provided.

Figure 2:
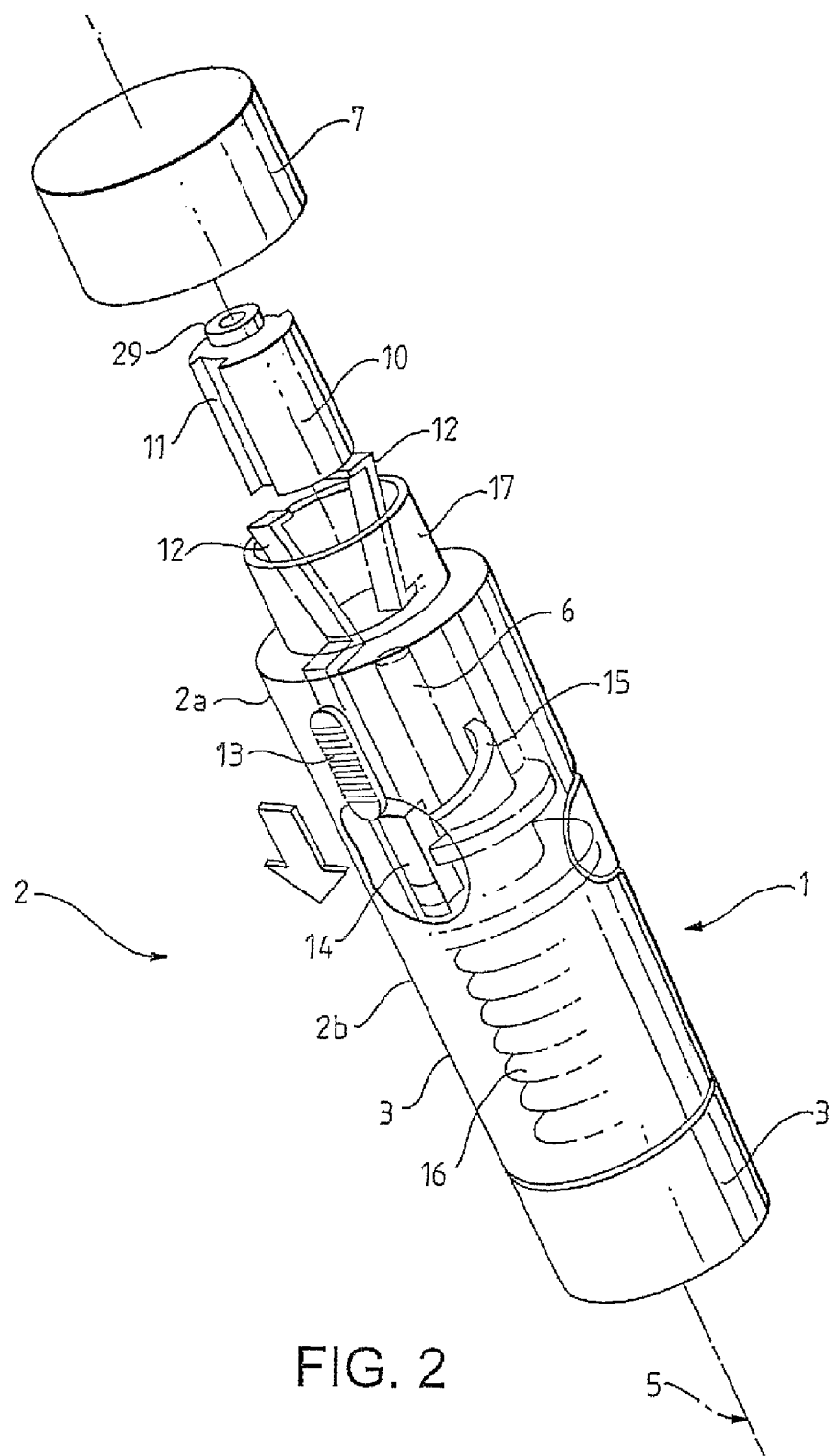
FIG. 2 shows a device including container cartridge.

FIG. 2 shows a likewise cylindrically designed device 1 in which, after the removal of the protective cap 7, the container cartridge 10 is introduced from above into the inside of the device 1. To this end, the container cartridge 10 is guided along the axis of symmetry 5 in the direction of the pressure piston 6. The container cartridge 10 has on both sides a groove 11 which is then surrounded by the arms of the holding means 12. The nozzle or dispensing facility of the container cartridge is identified as feature 29. Via a movable button 13 which is moved by the user in the direction of the arrow, a transport carriage 14 is activated which moves the container cartridge 10 in the direction of the pressure piston. When the device is used, the compression spring 16, in cooperation with a clamping element 15 (drive flange), ensures the rapid movement of the pressure piston 6 along the axis of symmetry in the direction of the container cartridge 10. This has a stock cylinder, not represented in the drawing, into which the pressure piston 6 cuts during the release procedure and in the process, by advancing a stopper (container piston, not shown) fitted into the container 10, pushes the drug solution located in the stock cylinder through the dispensing facility (not represented in the drawing) located at the container cartridge 10. The aerosol passes out from the dispensing facility, i.e. in this case an atomization facility, via the mouthpiece 17 to the outside.

Figure 3:
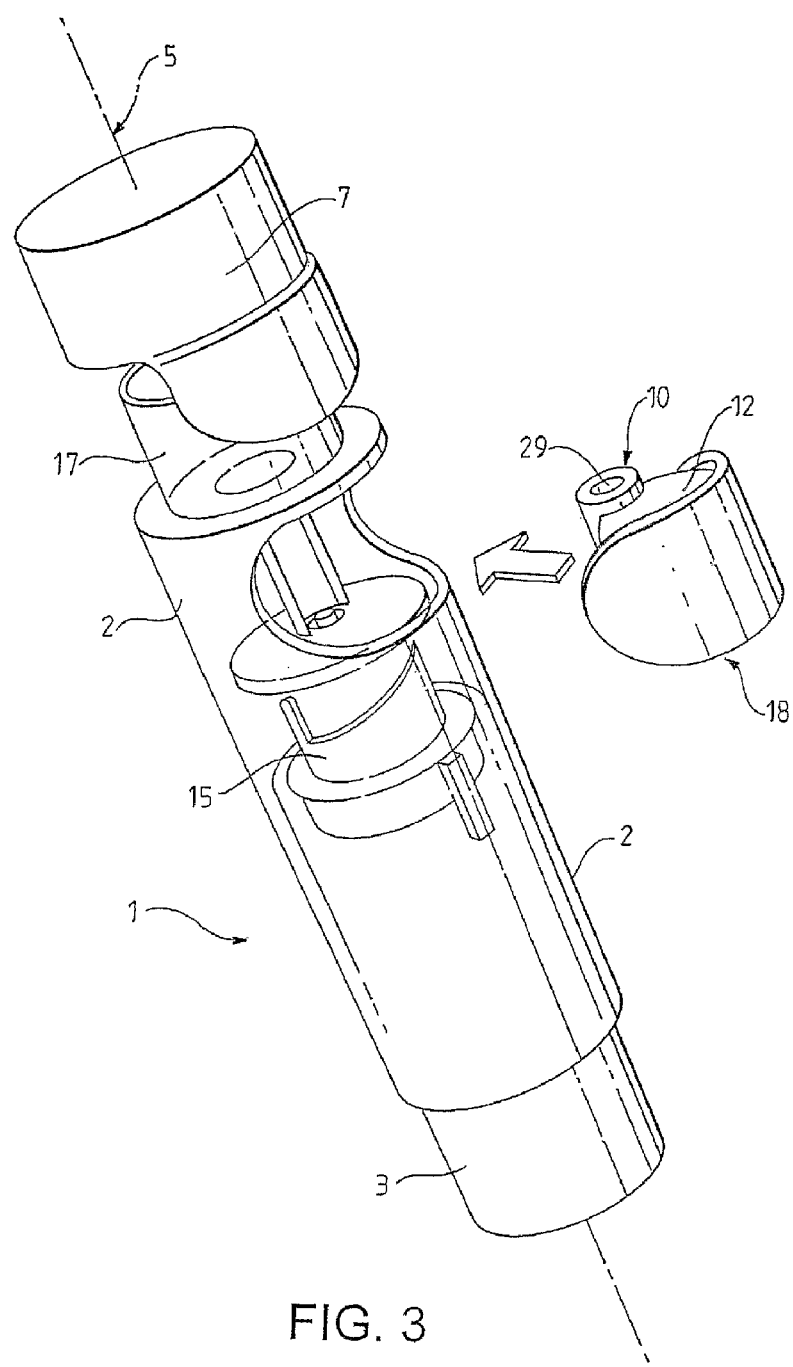
FIG. 3 shows a version with a removable grip for accommodation of the container cartridge.

FIG. 3 shows a version in which a part of the external wall of the device is cut out and forms a grip 18 which is provided with a holding means 12 for accommodating the container cartridge 10. The container cartridge 10 centrally has a dispensing facility 29. After the grip 18 is fitted with a new container cartridge 10, the grip is introduced in the direction of the arrow and is ready for use.

Figure 4:
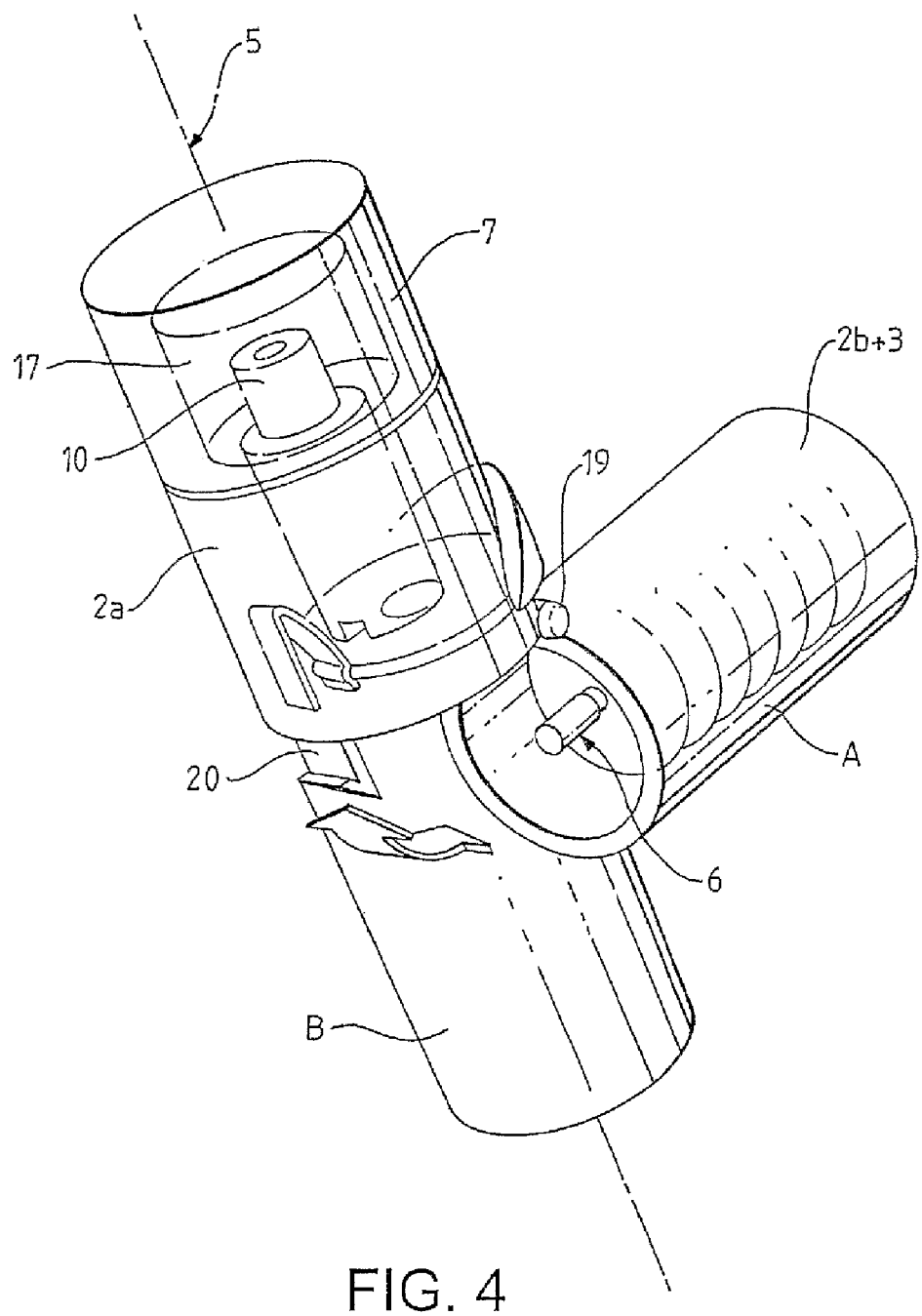

FIG. 4 shows a version in which the housing lower section 3 and the housing middle section 2b are shown simplified as a unit. The housing upper section 2a can be swivelled vis-à-vis the housing middle section by means of a hinge 19. To this end, the detent 20 is firstly operated in order that the housing middle section 2b together with the housing lower section 3 is transferred from its starting position A into its final position B. In the swivelled-out position of the housing middle section 2b plus housing lower section 3, the container 10 can be introduced into the housing upper section 2a or replaced. By manual pressure on the top end of the container cartridge through the mouthpiece 17, the container cartridge can be withdrawn again.

Figure 5:
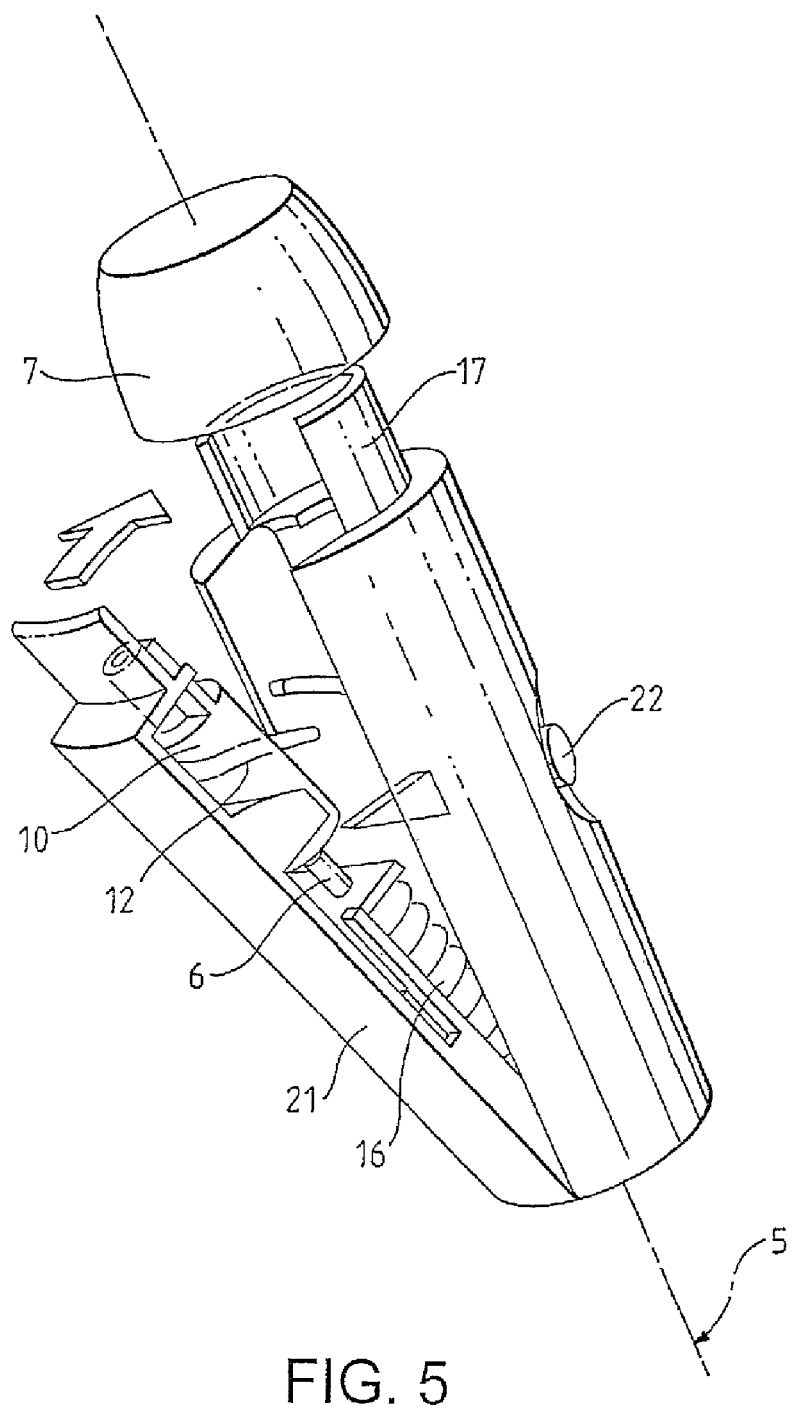
FIG. 5 shows a further version of the device.

FIG. 5 shows a version in which a part of the device 1 can be swivelled out as a swivelling flap 21. In the swivelled-out position, a view into the inside of the device is possible, and in FIG. 5 can be seen a compression spring 16 for moving the pressure piston 6 which, in the case of use, acts on the container cartridge 10 which is fixed in a target position by a holding means 12. After the device 1 is fitted with the container cartridge 10, the swivelling flap 21 is swivelled in the direction of the arrow to the axis of symmetry. The release is carried out via the release button 22.

Figure 6B:
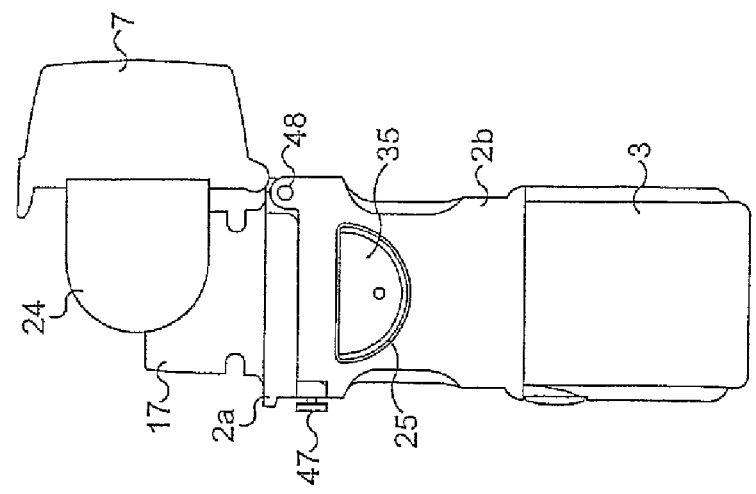
FIGS. 6a and 6b show the opening of the protective cap of the device.
Figure 6A:
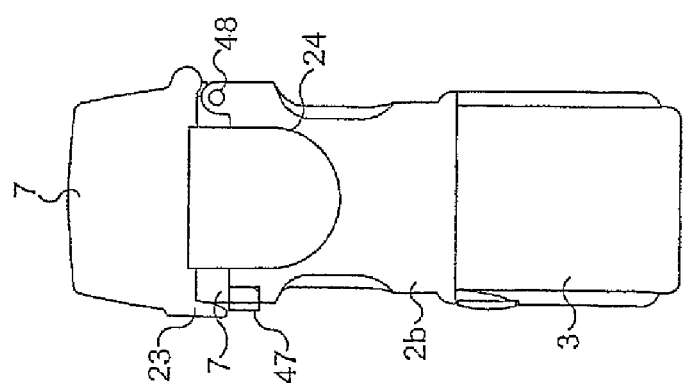

FIGS. 6a and 6b show the device with closed and opened protective cap 7. The housing upper section 2a is provided via a hinge 48 with a protective cap 7, which is initially swivelled outwards and thus reveals the mouthpiece 17. The protective cap 7 can lock into the closure position on the housing upper section 2a via the flap 23. The protective cap 7 also has a tongue-shaped section 24. This section 24 covers the tongue-shaped area 25 in which the release key 35 is located. In the closed state of the protective cap 7 the release key 35 cannot therefore be unintentionally pressed.

Figure 7:
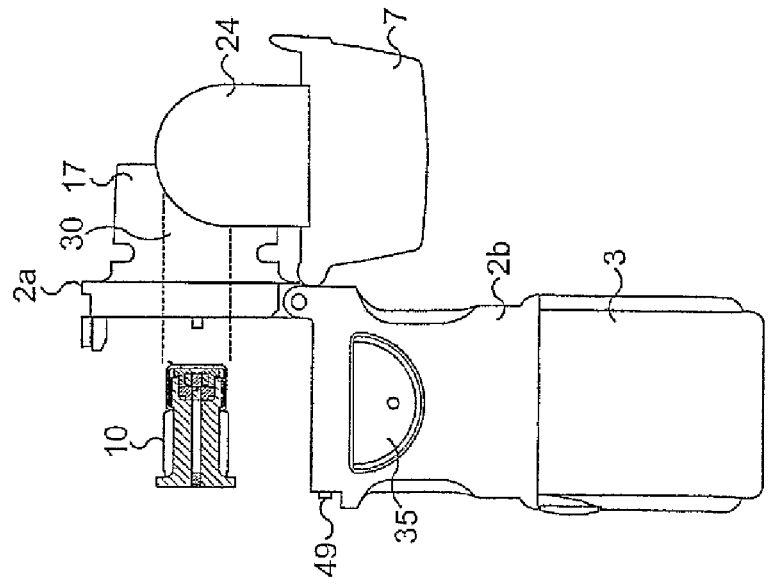
FIG. 7 shows a device with swivellable housing upper section 2a and its loading with the container cartridge.

The closure key 47 is located at the housing middle section 2b. If this is activated, the housing upper section can be swivelled up around the hinge 48 (FIG. 7). In this position can be seen the arrester bolt 49, connected to the closure key 47, which ensures that the housing upper section 2a can be opened only when the compression spring 16 is tensioned. In this position the container cartridge 10 can be pushed into the accommodation chamber 30 (dashed) (along the dashed marking).

Figure 8:
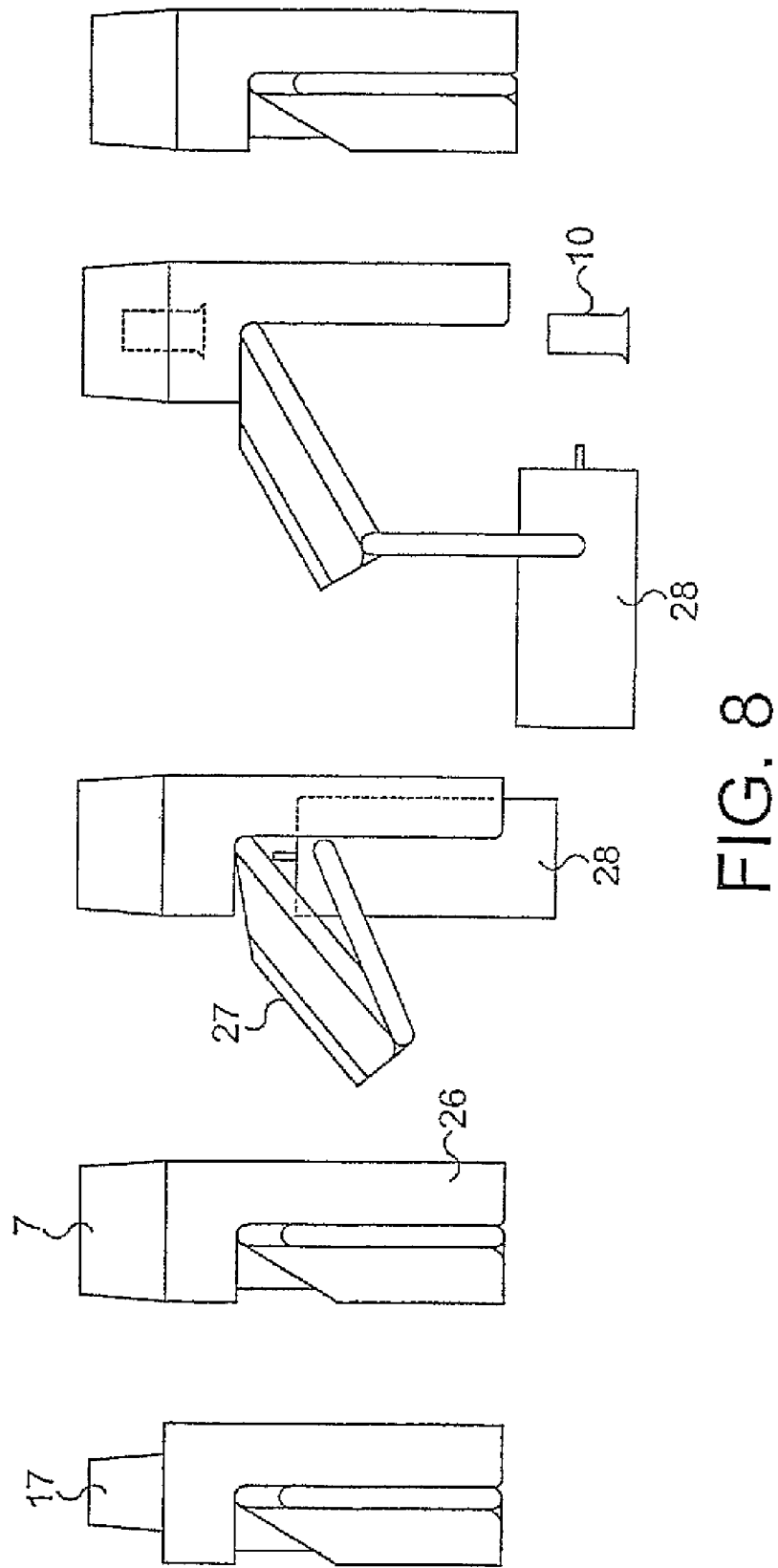
FIG. 8 schematically describes a further version of the device with swivellable arm.

FIG. 8 shows a version with a slightly L-shaped housing 26 with a mouthpiece 17 located thereon. A hinged arm 27 allows the mechanical drive unit 28 to be extended, and thus the container cartridge 10 to be introduced into or removed from the dashed-line accommodation chamber 30. After a suitable fitting of the device 1 with the container cartridge 10, the hinged arm 27 is pulled back, so that the device reaches its operating position.

Figure 9A:
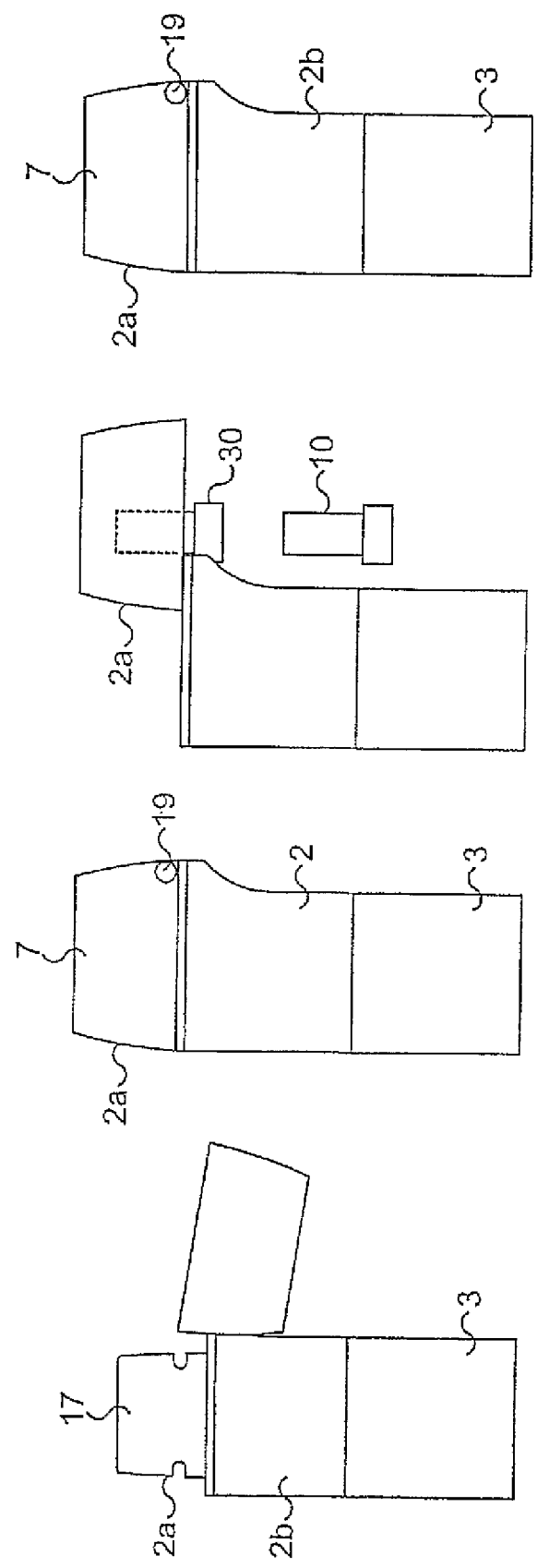
FIG. 9a schematically describes the process of loading the device with the container, the housing upper section 2a being rotated horizontally vis-à-vis the housing middle section 2b and housing lower section 3.

FIG. 9a shows a variant with a housing upper section 2a housed eccentrically rotatable. In this case the container 10 can be introduced into the accommodation chamber 30 only when the housing upper section 2a is rotated out laterally, i.e. horizontally vis-à-vis the housing middle section 2b. In this position the container 10 can be introduced into the dashed-line position, and then the additional part pushed back.

Figure 9B:
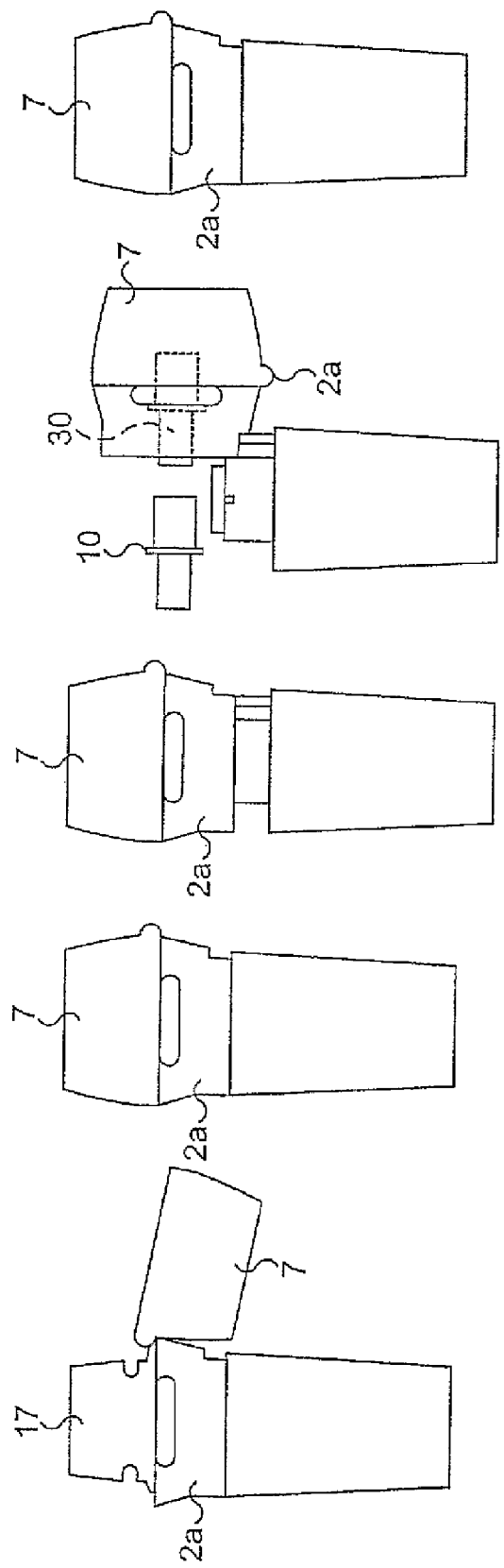
FIG. 9b schematically describes the process of loading the device with a swivelling mechanism with the container.

FIG. 9b shows in several snapshots from left to right the fitting of a device with a mechanism in which the housing upper section 2a can be opened only if it is first moved vertically against the housing middle section 2b.

Figure 10:
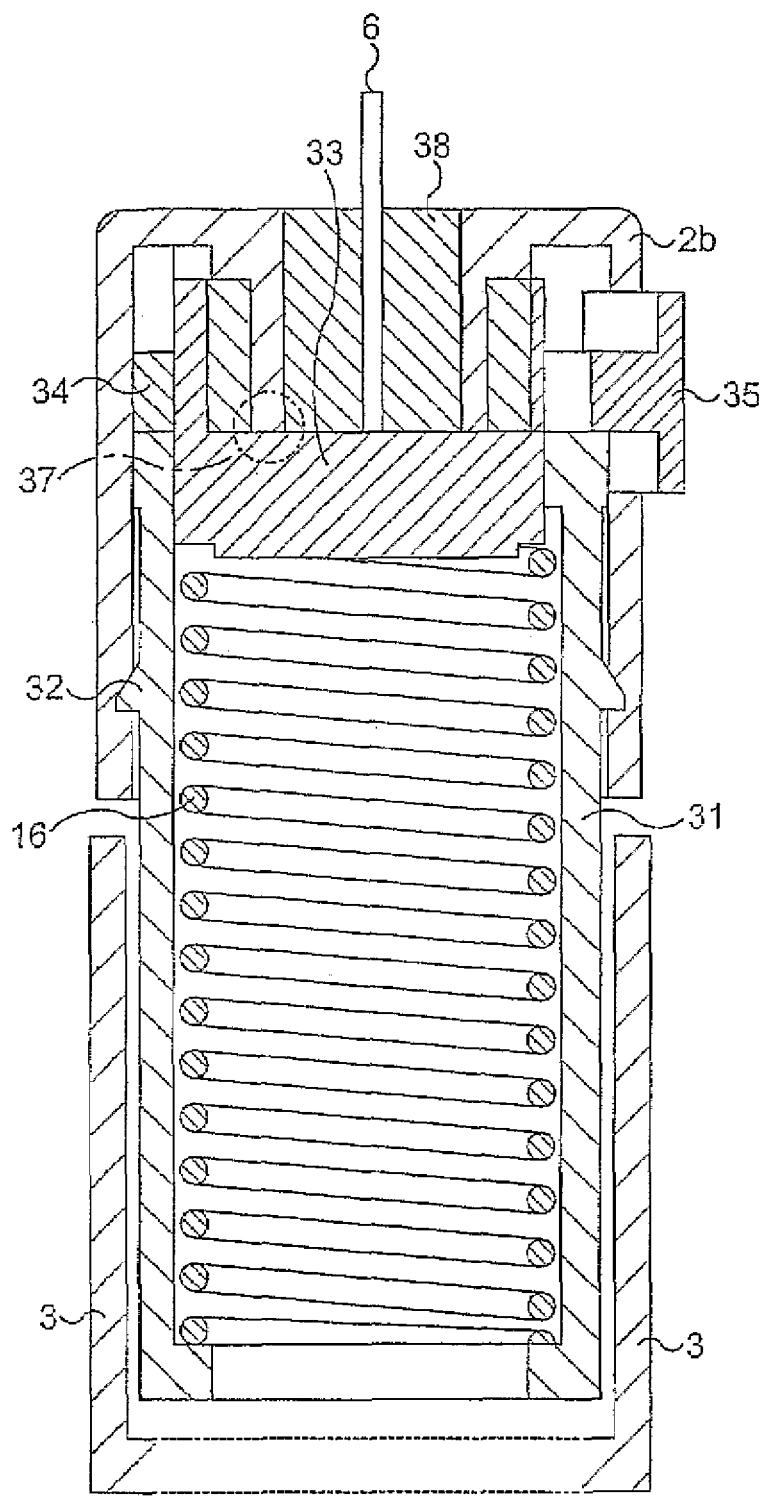
FIG. 10 and FIG. 11 describe the pressure-exertion means in the form of a locking clamping means.

FIG. 10 shows a longitudinal section through a locking clamping means. The upper cylindrical housing section 2, which in this case represents exclusively the housing middle section 2b, housing upper section 2a is not shown, grips over the compression spring housing 31 to which it is connected via snap catches 32. The snap catches 32 are attached to the outside of the compression spring housing 31 and extend over two circle segments lying opposite each other, each of roughly 30 degrees. They engage in a peripheral groove on the inside of the upper housing section 2. The housing lower section can be inverted over the compression spring housing and is connected via connection means (locking means) to the compression spring housing 31 removable but not rotatable against each other (the connection is not shown). The housing middle section 2b or the housing section 2 and the compression spring housing 31 are rotatable against each other.

Through the connection of the compression spring housing 16 to the housing lower section 3, the two housing sections 2 and 3 and in particular 2b and 3 are also rotatable against each other. Located in the compression spring housing 31 is the compression spring 16, which generally is already pretensioned when the two housing sections are put together. The compression spring 16 rests on a peripheral projection at the lower end of the compression spring housing 31 and on the drive flange 33, which is arranged movable in axis-parallel manner between the upper housing section 2 and the compression spring housing 31 and for its part presses against the upper housing section 2. The pot-shaped drive flange 33, which carries the pressure piston 6, projects into the upper housing section 2. The ring-shaped locking member 34 encloses the drive flange 33. The release key 35 attached to the locking member projects laterally from out of the upper housing section.

In the case of a screw sliding gear, the collar of the pot-shaped drive flange 33 generally contains two saw-tooth-shaped recesses, on which two saw teeth in the upper housing section glide (not shown). Upon rotation of the upper housing section 2 against the housing lower section 3 and thus against the compression spring housing 31, the drive flange 33 is pressed against the force of the compression spring 16 further into the compression spring housing 31. As soon as the upper edge of the drive flange 33 has been pushed far enough down through the locking member 34, the ring-shaped locking member 34 moves perpendicular to the housing axis between the upper edge of the drive flange and a ring-shaped projection 34 in the upper housing section 2 and holds the drive flange 33 and the compression spring 16, additionally tensioned by the movement of the drive flange, firmly in the reached position.

The average compression spring force is 10 to 150 N. Between the upper and the lower resting position of the drive part, the compression spring force changes by roughly ±10% of the average compression spring force.

By pressing the release key 35 the ring-shaped locking member 34 is pushed back perpendicular to the housing axis, as a result of which the path of the drive flange 33 is freed. The compression spring 16 pushes the drive flange 33 up for a predetermined distance and thus operates the pressure piston 6, connected to the drive flange 33, which is guided in the guide cylinder 38.

Figure 11:
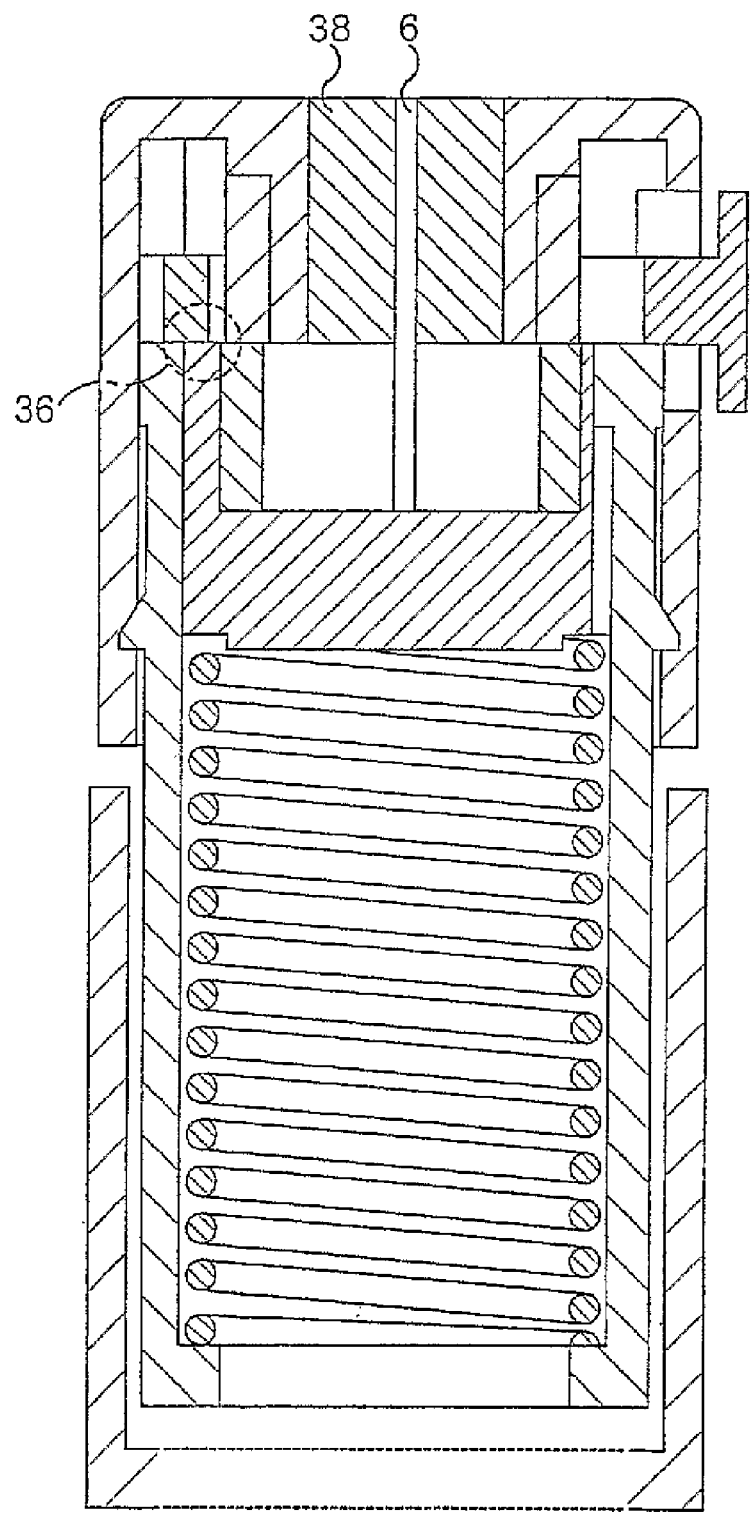

In FIG. 10 the locking clamping means is shown with the drive flange 33 in its upper resting position and with the locking member 34 released. FIG. 11 shows the locking clamping means with the drive flange 33 in its upper resting position and with the locking member 34 engaged. The stop 36 is the path limit for the drive part 33 in its lower resting position, the stop 37 is the path limit in its upper resting position. By rotating the two housing sections against each other, the position according to FIG. 10 changes into the position according to FIG. 11. By pressing the release key 35 the position according to FIG. 11 changes into the position according to FIG. 10.

Figure 12:
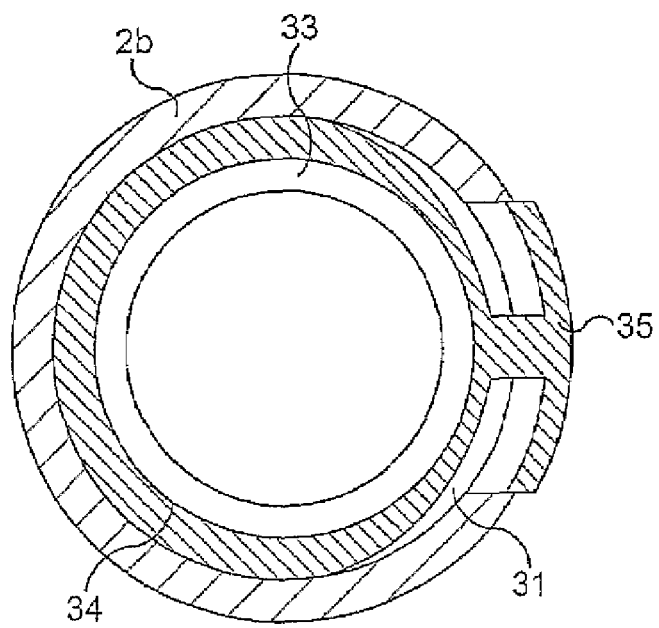
FIGS. 12 and 13 show the locking mechanism.
Figure 13:
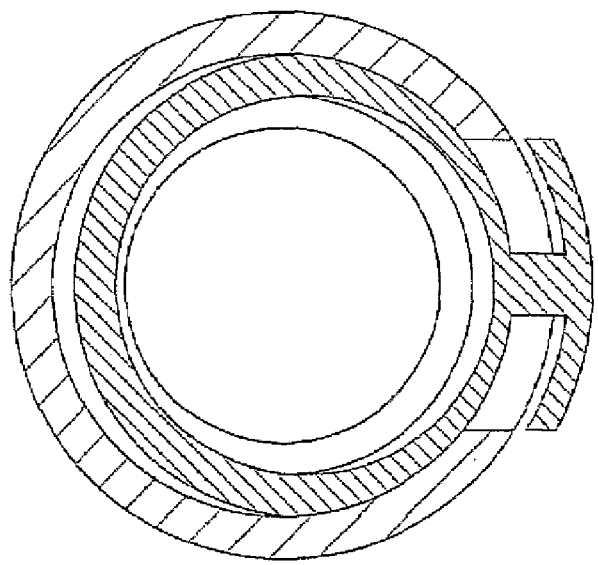

FIGS. 12 and 13 show a cross-section through the locking clamping means in the middle of the ring-shaped locking member, FIG. 12 corresponding to the position of the locking clamping means according to FIG. 10 in released position of the locking member 34 and FIG. 13 corresponding to the position of the locking clamping means according to FIG. 11 in engaged position of the locking member 34.

As already described, the re-usable part of the invention builds on the Respimat® technology. This part comprises a device with a) means for the respective introduction and removal of the container cartridge containing the drug into and from the inside of the device and b) means for the exertion of pressure on the container cartridge. This device builds on the principle as described by WO 97/12687 and its FIG. 6.

Preferably this device is similar to a cylinder in form and has a handy size of less than 9 to 15 cm long and 2 to 4 cm wide, so that the patient can carry it with him at any time.

It has a bottom-side end and lying opposite a top-side end. The top-side end defines the direction "to the top", the bottom-side end the direction "to the bottom". The top part has at its upper end an opening through which the liquid to be dispensed emerges from the device.

Preferably the device consists of at least three housing sections, a) a bottom-side housing lower section, b) a housing middle section and c) a top-side housing upper section.

If the two sections housing middle section and housing upper section form a structural unit or differentiation between the two sections is not necessary in the context, both are summarized as housing upper section.

The housing upper section open to the top can be sealed by a lid or a cap. This lid/cap can be an integral constituent of same or represent an element separate from it.

The housing upper section is preferably connected rotatable or swivellable with the housing middle section.

The housing lower section can be fitted onto the housing middle section in axial direction or connected to it.

The housing middle section preferably contains a spring which is tensioned against the housing middle section via a rotational movement of the housing lower section.

The housing upper section serves to accommodate the container and contains corresponding means.

The housing upper section has, parallel to the longitudinal axis of the device (=vertical direction) a continuous, preferably tubular, i.e. cylindrical bore. An optionally cylindrical cavity is thereby developed which is open on two sides. This cavity is developed to accommodate the container cartridge and within the framework of this description is also called container accommodation chamber or accommodation chamber in short. Alternatively it is called housing opening.

The container cartridge can be pushed into and withdrawn from the accommodation chamber manually or via a transport means. The accommodation chamber is preferably designed such that the container cartridge is accommodated in a precisely fitting manner, i.e. the container cartridge is intended to be able to carry out no or nearly no cross-movement in the inside itself. If the container cartridge is for example a bottle-like container cartridge, i.e. a container with belly, shoulder and head regions, the inside of the accommodation chamber is accordingly developed complementary thereto, i.e. this bottle shape is copied as a negative form. In all versions of the invention it must be guaranteed that the container is at least briefly firmly connected to the accommodation chamber in order that the container, upon exertion of pressure, is not hurled out of the accommodation chamber.

The two openings of the accommodation chamber lie opposite each other, one pointing towards the bottom of the device and when the device is closed touching the lid of the housing middle section. The other opening points towards the top part and preferably opens out into a projection, likewise open to the top, straight and tubular, which is developed on the top side of the housing upper section and whose vertical axis is preferably also developed parallel to the longitudinal axis of the device. That is to say, the vertical lying on the opening plane of the tube lies parallel to the longitudinal axis of the device. This projection can be a mouthpiece for an inhaler, an adapter for an eye bath or the like, or such a device can be connected to the projection. Such an adapter for an eye bath is described in PCT/EP0207038, to which reference is hereby expressly made. A mouthpiece is described for example in FIGS. 6 a/b of WO 97/12687, reference to which is also hereby expressly made in this connection.

Through the top-side opening of the accommodation chamber an aerosol emerging from the container cartridge can leave the device through the tubular projection. The container cartridge preferably fits precisely into the accommodation chamber.

In one version a transport means can be developed in the upper housing section or attached to the upper housing section, in particular a carriage or a transport carriage, into which the container cartridge is placed and which then transfers the container cartridge into its end-position in the accommodation chamber.

In a further version of the invention it can be provided that a part of the upper housing wall is a constituent of a removable grip which is provided with holding means for accommodating the container. Through the removal of a part of the housing wall an opening forms in this way through which the container can be introduced into the inside of the device. This removable part of the housing wall is provided with a suitable holding means with which an exact positioning of the container into its target position is particularly easily and quickly possible.

In other versions in which the housing middle section and the housing upper section can likewise be inseparably connected to each other and thus represent a structural unit, the container cartridge can be introduced into the accommodation chamber only from above, from the latter's top-side end. Also in this case the bottom-side end of the container cartridge points towards the bottom-side end of the accommodation chamber. The container cartridge can be connected firmly to the accommodation chamber via a thread, in order that it cannot be hurled out of the accommodation chamber during the exertion of pressure. In this case the container cartridge carries e.g. an external thread and the accommodation chamber a complementary internal thread. Such a closure can also be developed as a bayonet closure, or corresponding holding means are developed on the accommodation chamber.

In further versions which contain no such transport means for the container or in which the container cartridge can be inserted into the accommodation chamber not from above, but only from below, the housing upper section can be connected at least partially releasable to the housing middle section. In such a case the two sections are at any rate connected to each other such that the housing upper section can be removed from the housing middle section such that the bottom-side opening of the accommodation chamber is accessible. At the same time the device includes closure means which ensure that this opening mechanism can only be carried out deliberately by the user of the device and a chance separation of the housing upper section from the housing middle section during the use of the device is not possible.

In such a version it can be provided that, for the introduction of the container, the housing upper section is swivelled eccentrically rotatable or swivellable about the housing middle section. Through the swivellable design with the help of e.g. a hinge or swivel joint the whole device opens and the inside of the device becomes accessible. In this state the container cartridge can be introduced into the bottom-side opening of the accommodation chamber in the inside of the device. The advantage of this version is that the hinge or the swivel joint well illustrates the mode of operation of the mechanism and the opening is thus self-explanatory. Because of the clear operating zones, a single-dose container located in the accommodation chamber immediately becomes visible after the opening and the manner in which the container cartridge has to be replaced is clear.

In all these cases with a housing upper section mobile vis-à-vis the housing middle section, the bottom-side opening of the accommodation chamber for the container can lie in the bearing surface of housing upper section and housing middle section or touch or almost touch the housing middle section.

The opening mechanism can be such that the housing upper section is connected on the outside via an eccentric swivel joint to the housing middle section. A rotary movement of the housing upper section in the cross-plane defined by the longitudinal axis of the device thereby becomes possible, i.e. a horizontal rotary movement in which the axis between the bottom-side end of the housing upper section and its top-side end always remains aligned parallel or roughly parallel to the longitudinal axis of the device.

It can also be provided that the housing upper section is developed as a swivelling flap.

In such a case, the housing upper section can be swivelled away from the housing middle section, i.e. the axis between the bottom-side end of the housing upper sections is moved as if it were turned upside down. The swivelling flap comprises e.g. a hinge which is preferably arranged at the lower end of the housing upper section In versions in which the housing upper section must firstly be opened before the container cartridge can be inserted, it is advantageous if the housing upper part cannot be separated completely from the housing middle section. This facilitates the operability of the device.

The cavity of the accommodation chamber is such in such versions that therein the container can be pushed only from below into the accommodation chamber. In this case the head region of the container cartridge is aligned in the direction of the top-side opening and the base region of the container cartridge points in the direction of the housing lower section. In the head region of the container lies the dispensing facility—which optionally represents an atomization facility, in the ideal case a nozzle. This can still lie inside the container accommodation chamber, end in the accommodation chamber or project through the top-side opening. The analogous case applies to the bottom-side end of the container cartridge. The bottom of the container cartridge preferably ends plane with the bottom-side opening of the accommodation chamber.

The accommodation chamber and the container are preferably designed such that the container can be pushed into the accommodation chamber only from below but not from above. Optionally developed on the container and/or the accommodation chamber are further means which prevent the container from being able to be pushed fully through the accommodation chamber. These means can consist of guide rails, guide grooves or guide indentations along the vertical axis of the chamber, of stops and the like. The container then has means contrary thereto. By way of example, the bottom-side opening of the accommodation chamber can e.g. in the initial area have one or more recesses and the container has, bottom-side, corresponding projections which fit into the recesses. Also, at the bottom-side opening of the accommodation chamber e.g. a recess in the form of a peripheral ring (collar) can be developed. In longitudinal section the cavity of the accommodation chamber is thus T-shaped. The container can then be developed precisely complementary thereto, i.e. likewise T-shaped in longitudinal section, the "T-beam" forming the bottom of the container. In this case the container can have, bottom-side, a ring or collar which thickens the outer casing so that it fits into the area of the recess, but no longer into the area with the smaller diameter of the accommodation chamber.

In other versions the container and the accommodation chamber taper to the upper end.

Also, at the top-side end of the accommodation chamber, a stop can be developed which ensures that e.g. the container cannot be pushed fully through this opening. The stop, e.g. in the form of a tapering opening or a peripheral edge developed to the inside, can be developed so that the top end of the container or, in the case of a bottle-shaped container, its shoulder strikes against the stop. Since, according to the invention, the dispensing facility preferably forms the top end of the container cartridge, i.e. in the case of a bottle-like container cartridge the neck of the bottle, such a stop can lead to the dispensing facility being held by the stop or else the container cartridge is held underneath the dispensing facility in the shoulder area and the dispensing facility itself projects through the opening into the tubular projection.

Preferred are versions in which the container can be pushed fully into the delivery chamber only from below. With versions in which the container can be pushed at least to a small extent into the accommodation chamber coming from the top opening, locking elements are developed on the container and/or the accommodation chamber which prevent the container from being fully pushed in. It must be borne in mind that the container cannot be pushed so far into the opening that pressure can be transmitted from the pressure exertion device to the container.

A preferred version has, for the housing upper section as further component, a swivellable and arrestable protective cap which covers at least the tubular projection and thus the top-side opening of the accommodation chamber or the upper lid area. It is thus guaranteed that the areas of the device that lie further within are protected. This is important in particular if the device is kept in the trouser pocket or a handbag. In order that the protective cap itself does not unintentionally leave its arrested position, it can provided that the protective cap has a tongue-shaped section which can be locked in a tongue-shaped recess of the housing. This protective cap can be developed so that in the closed state it covers the release button of the device which is developed in the housing middle section, and thereby prevents an unintentional release.

The housing middle section accommodates an energy storage means for the generation of pressure on the container and a mobile element which is moved by the release of the stored energy and thereby directly or indirectly exerts pressure on the container cartridge or on the liquid located in its inside.

The energy storage means is preferably an elastic element, for example a compression spring (compression spring). However, the pressure can also be exerted by means of other elements for example a motor.

In the case of a compression spring or coil spring as energy storage means this can be arranged in a compression spring housing which is located at least partly in the housing middle section and optionally is connected to this via snap closures. Preferably, at least a part of the compression spring housing projects bottom-side from out of the housing middle section, i.e. the compression spring housing is longer than the housing middle section. In this case the compression spring housing or a part of it can be housed rotatable by means of a swivel joint in order to tension the compression spring via a rotary movement and a locking clamping means. The compression spring can then be relaxed again by a release mechanism.

The mobile element can be a piston (pressure piston) which is moved by the compression spring movement itself. It is pushed into the accommodation chamber by the relaxing of the compression spring and exerts pressure on the container.

The pressure piston can be connected to the compression spring via a drive flange, in this case being firmly connected to the drive flange. The pressure piston is preferably guided over a bore in the otherwise closed lid area of the housing middle section. Optionally, the top-side part of the pressure piston can be guided in a cylindrical element (guide cylinder) which is developed in the lid area of the housing middle section. In the tensioned state of the compression spring the pressure piston is wholly in the housing middle section. In the relaxed state the upper end of the pressure piston is located in the housing upper section and pierces a container cartridge situated there. The pressure piston has a vertical movement play of up to some centimeters, preferably less than 2 cm, particularly preferably between 0.1 and 1.5 cm.

The pressure piston can be developed as a hollow or solid piston and after activation exerts high mechanical pressure on the container.

The locking clamping means contain the said compression spring, preferably a cylindrical helical compression spring, as storage means for the mechanical energy. The locking clamping means preferably have a vertical longitudinal axis. In the following a version of the locking clamping means is described. The compression spring acts on a drive flange as spring piece, the movement of which is determined by the position of a locking member. The path of the drive flange is precisely limited by an upper and a lower stop. The compression spring is preferably tensioned via a force-transmitting gear system, e.g. a screw sliding gear system, by an external torque which is produced upon the rotation of the housing middle section against the compression spring housing in the housing lower section. In this case the housing middle section and the drive flange contain a V-gear system which is single- or multi-gear.

The drive flange is pressed against the force of the compression spring into the compression spring housing.

The compression spring can be kept in the tensioned state via a locking member.

This locking member has meshing locking surfaces and is arranged in the form of a ring round the drive flange. It consists e.g. of a ring made of plastic material or metal. The ring is arranged in a plane perpendicular to the atomizer axis and is housed mobile in this plane. After the tensioning of the compression spring the locking surfaces of the locking member move into the path of the drive flange and prevent the relaxing of the compression spring. The locking member is released by means of a key (release key), which is likewise developed at the housing middle section. This release process can be effected by pressing the key. The release key is connected or coupled to the locking member. For the release, the release key is moved parallel to the ring plane, preferably into the atomizer; in the process the ring will move in the ring plane. Design details of the locking clamping means are described in WO 97/20590, as regards the locking mechanism reference is made to FIG. 3 following this patent application. Alternatively to this the ring can be radially elastically deformable. In this case the ring is deformed when the release key is moved for the release. A movement of the ring in the ring plane is not necessary.

At the housing upper section and/or housing middle section means can be developed which connect the two sections to each other so that a separation, swivelling open etc. of the two sections during the pressure release is not possible.

In such cases the housing middle section is connected to the housing upper section via a closure which prevents the housing upper section from unintentionally opening.

To this end the housing middle section can have means of blocking (blocking means) the release mechanism which prevent the exertion of pressure being released when the device is open, i.e. as long as the housing upper section is not firmly connected to the housing middle section.

The housing middle section can also have means which prevent the device from being opened (the housing upper section from being opened) as long as the compression spring is relaxed, and the piston thus projects into the housing upper section (closure arrest means).

A preferred version has both blocking means and closure arrest means.

Preferably the blocking means are such that they prevent the movement of the locking member (see locking clamping means) in the direction into which the locking member is forced in order to relax the compression spring. Such a means can be a spring-loaded locking bolt which, seen from horizontal plane from the push button, lies vertically behind the locking member. In the opened state of an e.g. tiltable housing upper section a spring forces the locking bolt somewhat upwards out of the housing middle part. In the closed state the housing upper section forces the locking bolt against the spring back into the starting position. The locking bolt can be cylindrical, square and the like and is either so configured or so guided that the locking bolt prevents the horizontal movement of the locking member that is necessary for the release when the device is open and releases the locking member when the device is closed. For example, the locking bolt can have recesses which, only in the closed state of the device, free the path of the locking member for the relaxation of the compression spring.

The locking bolt can, in alternative versions, also arrest the release key so that this can be pressed in only when the device is closed. In such a version, the locking bolt can again have recesses. Also in this case the locking bolt prevents a movement of the release key until the locking bolt is pressed and thereby frees the path for the release key.

Analogous blocking means can be developed for versions of the device in which the housing upper section is housed eccentrically rotatable vis-à-vis the housing middle section.

In these cases the locking bolt is pressed via the torque back into its starting position, and thus frees the path for the locking member or the release key.

The closure arrest means are preferably coupled with the closure between the housing upper section and housing middle section. It prevents the housing upper section from being opened as long as the pressure piston projects into the housing upper section, i.e. the compression spring is relaxed. It then controls the release of the closure key which maintains the closure between the two housing sections (closure key).

The closure key is then coupled with an arrester bolt. The latter is mechanically connected to the pressure piston. For example, it can be housed horizontal or at least skewed to the longitudinal axis of the pressure piston. If the compression spring is tensioned, the pressure piston is located inside the housing middle part. The arrester bolt can then be pushed, by a spring, above the pressure piston into its guide channel. In this position the closure key is released so that the closure mechanism between housing middle section and housing upper section can be opened.

In alternative versions, the arrester bolt does not shift into the guide channel of the pressure piston, but along a recess of the pressure piston. The recesses on the pressure piston free the path for the arrester bolt only in the tensioned state of the compression spring. In the relaxed state of the compression spring on the other hand, the arrester bolt blocks the pressure piston so that the release movement of the arrester bolt is thus prevented as long as the pressure piston is not wholly sunk into the housing middle section.

If the device is relaxed, the pressure piston moves from the bottom to the top and in the process pushes the arrester bolt back into its starting position in which it blocks the closure key. For this purpose, the tip of the pressure piston or the recess can have diagonals and the arrester bolt has the corresponding complementary diagonals.

The housing lower section is located underneath the housing middle section. In preferred versions it is pushed axially over the compression spring housing until the housing lower section and the housing middle section touch, while the compression spring housing is located inside the space thereby formed.

The housing lower section is connected to the compression spring housing via a releasable connection, e.g. a plug-and-socket connection or unreleasable connection.

Upon operation of the device the housing middle section is rotated against the housing lower section, the housing lower section taking the compression spring housing with it. The compression spring is compressed via the screw sliding gear system and tensioned, and the locking means automatically engage. The angle of rotation is preferably a whole fraction of 360 degrees, e.g. 180 degrees. Simultaneously with the tensioning of the compression spring the drive part in the housing middle section is moved a predetermined distance and the pressure piston guided by the cylinder in the lid area of the housing middle section is drawn back. Further design details are disclosed in the PCT applications WO 97/12683 and WO 97/20590, to the contents of which reference is hereby made.

FIGS. 14*a* to *e* show the container cartridge 10 according to the invention. Located top-side is the dispensing facility 29 which is connected to the outlet of the stock cylinder 40 and can conduct a liquid. The bottom-side end of the stock cylinder 40 is closed by the container piston 39.

The opening of the dispensing facility 29 is closed by an upper sealing means 58. The container piston 39 is closed to the outside by the lower sealing means 59. The dispensing facility 29 is held by one or more holders 60.

Figure 14A:
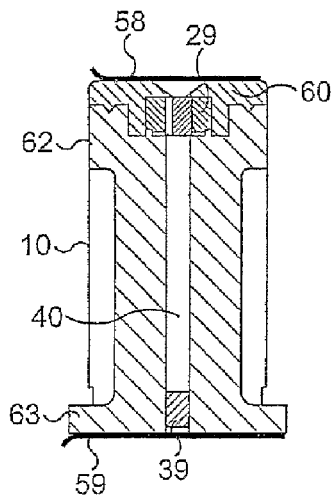
FIGS. 14a to 14e show the container cartridge according to the invention.
Figure 14B:
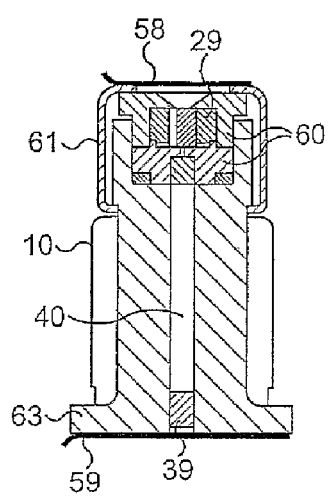
Figure 14C:
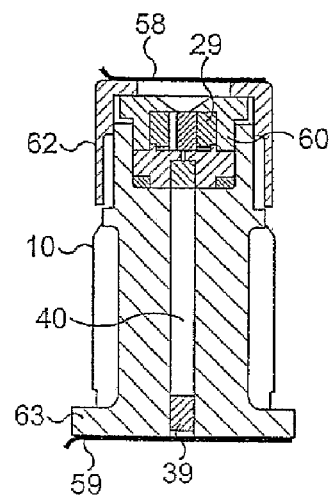
Figure 14D:
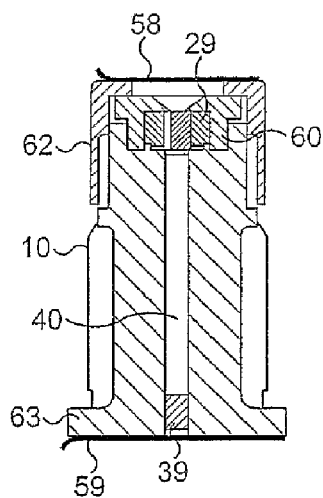
Figure 14E:
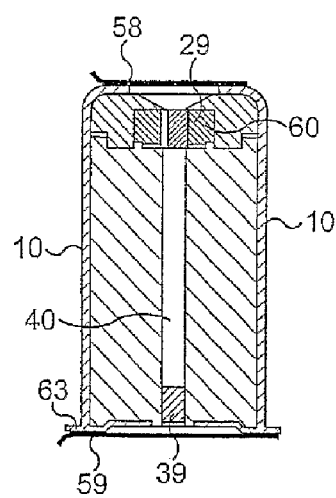

In FIG. 14*a* the holder 60 is connected in form- or material-locking manner (e.g. welded or glued) to the container cartridge 10. In FIG. 14*b* it is held by a crimping sleeve 61, in FIG. 14*c* by a screw cap 62. In FIG. 14*e* the crimping sleeve 61 surrounds the container from the top area to the bottom. In all the versions shown the baseplate 63 is wider than the container belly. The holding means, such as crimping sleeve or screw cap, are such that they free the opening of the dispensing facility 29, i.e. do not cover this opening.

In all the illustrated versions the container cartridge is pushed bottom-side into the housing upper section until the baseplate 63 encounters the edge delimiting the bottom-side opening of the accommodation chamber 30.

The container cartridge is a dimensionally stable container which cannot be deformed by manual pressure, i.e. it is plastically deformable along neither the longitudinal axis nor its transverse axis. Preferably the piston is conceived such that it is dimensionally stable vis-à-vis a pressure difference from inside to outside of 49 to 599 bar, preferably 149 to 299 bar.

As already stated, the container or the single-dose cartridge is firmly connected as a disposable part to a facility for the dispensing of a liquid, for example a nozzle. That is to say, this facility is an integral constituent of the container. Thus the device for the exertion of pressure (the device) no longer needs its own dispensing facility, so that this device for the exertion of pressure as such is structurally simplified vis-à-vis the devices of the Respimat® mark known from the state of the art.

The container cartridge is preferably of cylinder-like or bottle-like design. The container can also be designed in cartridge form or in imitation of the shape of an inhalation capsule. The outer shape of the container need not be a faithful copy of a cylinder, a bottle, cartridge or inhalation capsule, but preferred versions resemble one of the objects. The shape of an inhalation capsule can be seen in the figures of EP 1100474, reference to which is hereby made. Such capsules can be described as cylinder-like structures with two semicircular ends. The container cartridge has a bottom-side and a top-side end, the bottom-side end pointing towards the bottom-side end of the device for the exertion of pressure when the container is fitted into this device. Correspondingly, the top-side end of the container cartridge points towards the top-side end of the device for the exertion of pressure.

In a preferred version, the container cartridge has a rotation-symmetrical outer contour which tapers from the bottom to the top. The diameter preferably tapers in steps. Most preferably, at least one such step is developed such that the container has a shoulder. Such a container can e.g. be of bottle-like design with foot part, belly part, shoulder and top part. The foot region preferably has a collar running in peripheral manner around the casing or is broadened in the bottom region. This can be achieved using a corresponding baseplate. The advantage of this shape is that the container can be pushed in correct orientation only and only from the bottom opening into the accommodation chamber into which the container fits precisely.

In alternative versions, the cross-section of the container vertical to the longitudinal axis is triangular, square or polygonal or has another non-rotation-symmetrical shape. The advantage of these shapes is that the container must be very deliberately pushed into the accommodation chamber by the user, so that errors are avoided. In such a version, the cross-section can e.g. have the shape of a circle sector, i.e. a structure with three corners, two straight lines and a curved side. The angle between the two straight sides can have any values between greater than 0 degrees and less than 360 degrees, values of 200 degrees to 300 degrees are preferred. Alternatively, the cross-section can be in the shape of a circle segment, i.e. a structure which has one straight line and an arc spanning the straight line, or a circle in which a piece is cut off parallel to the diameter. The height above the mid-vertical of the straight line can be greater than the radius of the circle on which it is based, the same size or smaller. The height is preferably greater than the radius. A tapering from the bottom to the top, optionally step-like, is also advantageous with these versions.

In other alternative versions, with the previously described containers, the baseplate of the container, which is broader compared with the rest of the container, itself has a circular cross-section.

In further versions, the cross-section of the container is round, whereas the baseplate (foot) of the container, which is broader compared with the rest of the container, has the previously described non-rotation-symmetrical cross-section.

The container cartridge is preferably a single-dose container or a single-dose cartridge. This container has a hollow cylinder to accommodate the fluid (stock cylinder), the actual stock chamber, which also functions as a pressure chamber during use. There can be located bottom-side in the stock cylinder a movably arranged element (movable container punch, e.g. in the form of a piston (container piston) or preferably a ball (container ball)), which seals off the fluid to the outside. The facility for the dispensing of the liquid is arranged at the top-side end of the container. The movably arranged container punch, the stock chamber and the dispensing facility are arranged in series so that a liquid which is located in the stock cylinder, i.e. in the stock chamber, is pressed through the dispensing facility when the container punch is pushed into the stock chamber by a force acting from outside. During use with the device for the exertion of pressure, the force acting from outside is the force which is exerted by the pressure piston on the container punch. In the case of a drug solution or suspension as stored liquid, this is fed to the atomization facility. This is preferably an atomizer nozzle which for its part leads to the nebulizing of the drug.

Optionally the bottom-side opening and the top-side opening of the stock cylinder can have a sealing means or several sealing means.

The sealing means of the bottom-side opening can be arranged either bottom-side of the container punch or in top-side direction. Preferably the container punch itself seals off the bottom-side opening. Optionally a sealing film is applied bottom-side to the bottom-side opening.

The sealing means of the top-side end can likewise be arranged in bottom-side direction, i.e. before the dispensing facility or after it, thus top-side. Preferably it is arranged top-side, i.e. the opening or the openings of the dispensing facility is (are) sealed, e.g. by a manually detachable sealing film.

Preferably it is provided that the stock cylinder inside the container has a supply stock capacity of at most 1 ml, capacities of at most 100 microlitres being preferred, e.g. for eye treatment, and capacities of less than 50 microlitres particularly preferred. For nasal application, capacities of up to 30 microlitres can be preferred and for pulmono-inhalative application capacities of up to 15-20 microlitres are most strongly preferred. This quantity of drug is sufficient for the administration of a single dose and avoids the use of a preservative, as desired.

In a preferred version the stock cylinder has a constant internal diameter over the whole longitudinal axis. The bottom-side and top-side openings are perpendicular to the longitudinal axis on the upper side or lower side of the stock cylinder. Both openings extend over the whole diameter of the stock cylinder.

The container preferably has a height of up to 4 cm, more preferably up to 2.5 cm, particularly preferably up to 2 cm. The stock cylinder has a corresponding length in its inside, with a corresponding ratio of length to cross-section, in order to provide the whole filling capacity. The diameter of the cross-section is preferably up to 5 mm, more preferably up to 3 mm and particularly preferably up to 2.5 mm.

The container punch lies with a precise fit in the stock cylinder and is preferably made from a plastic material. This can be for example: polytetrafluoroethylene, ethylene-propylene-dienepolymer, silicon, elastomers, thermoplastic elastomers, such as Santoprene® and others.

Preferably the container punch lies exclusively inside the stock cylinder and more preferably the bottom-side end of the container piston ends bottom-side in the container, i.e. the container punch does not project outwardly beyond the bottom of the container and therefore also cannot be accidentally moved during storage, transport and the like.

The container punch is dimensioned for a precise fit or approximately precise fit, so that it closes the stock cylinder tight on the one hand, but on the other hand can be moved into the stock cylinder when a force is exerted.

By precise fit or approximately precise fit is meant that the container punch occupies the stock cylinder according to the cross-section, optionally the diameter of the container piston that is responsible as regards the closure of the stock cylinder can be up to 5% wider than the diameter of the stock cylinder. By approximately precise fit is meant that this diameter of the container punch is slightly smaller than the diameter of the stock cylinder.

Preferably the container punch is developed as a container punch with precise fit. Such a variant can be of advantage when filling the stock cylinder, but also when guiding the container stamp through the stock cylinder.

The container punch can have a slightly greater external diameter than the internal diameter of the stock cylinder, especially when it is situated in the closure position inside the stock cylinder.

A better closure of the bottom-side opening is thereby achieved. In addition this has the advantage that the container punch completely empties the stock cylinder when the container punch is pushed through the stock cylinder.

In one version the container punch is a cylinder.

A cylindrical container punch can have a recess in the form of a cavity which is open to one side. The opening of the recess points towards the bottom-side opening of the stock cylinder, i.e. in the direction of the pressure piston. The internal diameter of the opening or of the recess is greater than the external diameter of the pressure piston of the device for the exertion of pressure. In cross-section the container piston then has the shape of a U optionally with edges developed as corners. The bottom of the recess forms the point on the container piston at which the pressure piston can engage in order to press the container piston in the stock cylinder. The advantage of this design and arrangement is that the container piston can taper slightly, because of the pressure of the pressure piston on the bottom of the recess, at the opposite end, that is on the side of the container piston which forms spear tips upon penetration of the reservoir. That is to say, because of the pressing of the pressure piston, there is a change in cross-section in the shape of the container piston from the U-shape into approximately a V.

A simplified passage of the container piston through the stock cylinder is thereby achieved. A further advantage of this change of shape, caused by the pressure of the pressure piston, of the container piston is a reduction in the pressure of the pressure piston on the walls holding the container piston, so that even a firmly seated container piston can be released and moved from the pressure piston without tilting.

In order to prevent a tilting of the container punch, guide facilities, e.g. guide rails or guide vanes etc., can also be developed at the container punch and/or the side wall of the stock cylinder.

To improve the sliding of the container punch through the stock cylinder, the container punch or the wall of the stock cylinder can be coated with a pharmacologically compatible lubricant. Such lubricants are known from the state of the art and include e.g. sorbitan esters, e.g. sorbitan trioleate, oleic acid, lecithin and other fatty acids, fatty alcohols, esters of fatty acids and the like.

In other structurally similar containers, the container punch can be part of the rigid and inflexible baseplate of the container. In this case the pressure piston penetrates the baseplate of the container and then presses into the stock cylinder. In such cases theoretical fracture points can be developed on the baseplate, so that the pressure piston can more easily push out the integrated container punch from the baseplate during the exertion of pressure.

In these cases the pressure piston can be dimensioned such that no liquid is forced out of the reservoir past the pressure piston bottom-side from the container.

In other versions the bottom-side opening of the stock cylinder is closed only by a flexible sealing means, e.g. a sealing film and the like. Preferably the sealing means are not indestructibly removable from the container. In this case the pressure piston assumes the function of the container punch.

Figure 15:
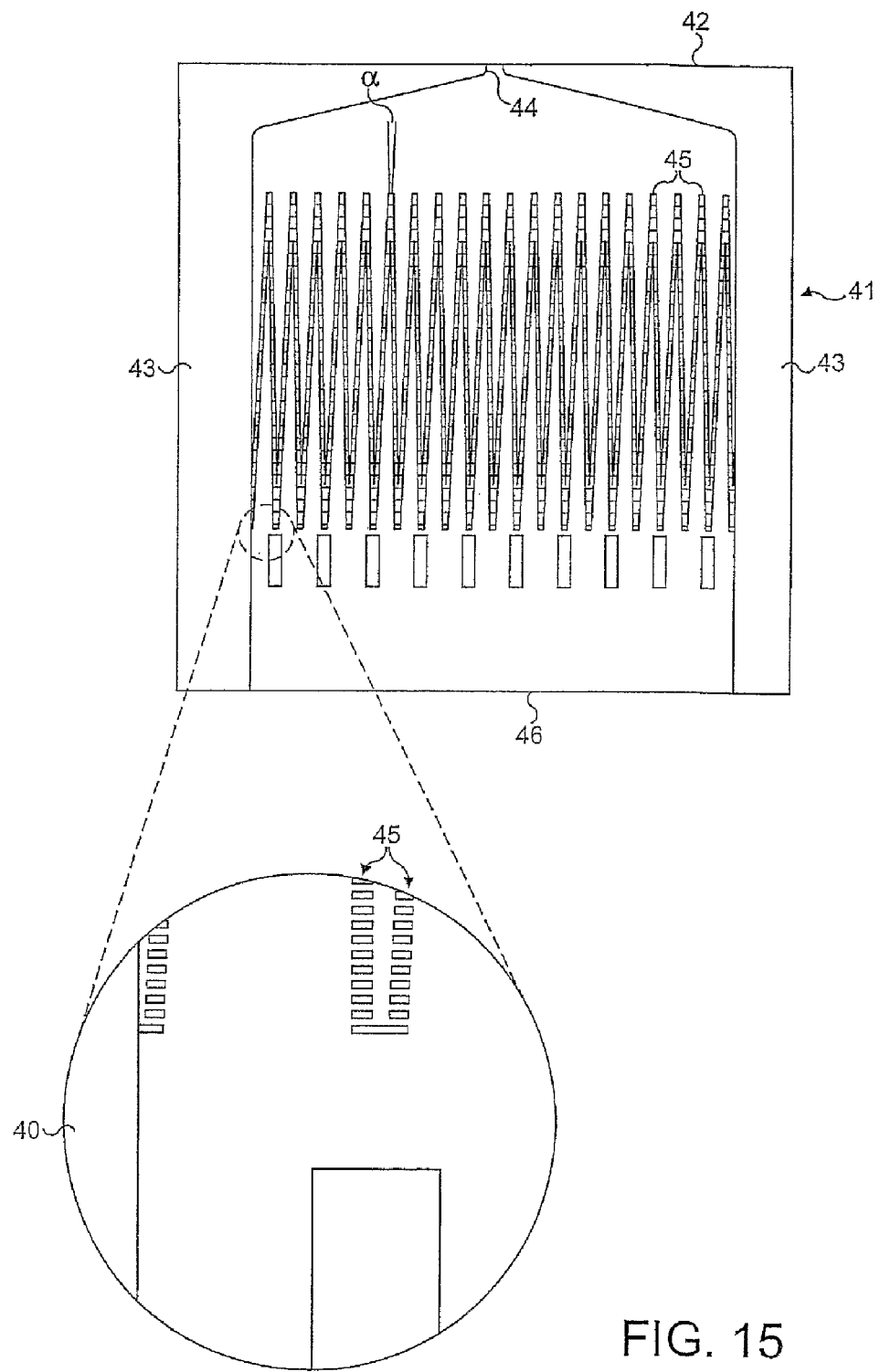
FIG. 15 describes a dispensing facility, preferably for the atomization of a liquid.

FIG. 15 shows a cross-section through the preferred nozzle structure 41. The figure shows the relief-like microstructure of the base part 42. The area 43 represents the non-etched part of the plate. The figure shows only one nozzle opening 44 instead of preferably two channels inclined towards each other with nozzle openings. The projections forming the zig-zag-configurated filter bear the reference number 45. The nozzle inlet side bears the reference number 46.

The dispensing facility, which can be an atomization facility and which is integrated with the container according to the invention, can be a special nozzle, as described for example by WO 94/07607, WO 99/16530 or the German patent application with the application number 10216101.1. Reference is hereby expressly made to all the documents.

In the simplest case the nozzle is a kind of perforated shutter, i.e. the nozzle represents a body with a single central continuous bore.

Another version of the nozzle is a body with at least two or more continuous bores which run parallel to each other or are inclined towards each either. In the case of bores inclined towards each other, the side with the acute angle forms the nozzle outlet side, the other side accordingly the nozzle inlet side. In the case of at least two bores the inclination angle is preferably 20 degrees to 160 degrees, preferably 60 to 150 degrees, particularly preferably 80 to 100°.

The nozzle openings are preferably arranged at a distance of 10 to 200 micrometres, more preferably at a distance of 10 to 100 micrometres, particularly preferably 30 to 70 micrometres. 50 micrometres are most strongly preferred.

The dimensions of the nozzle openings and nozzle channels correspond to those of the versions described in the following.

The nozzle can consist e.g. of glass, silicon, plastic material, such as PBT (polybutadiene terephthalate), PP (polypropylene), PC (polycarbonate) and others.

Another version of the nozzle is described in EP 0860210. In particular reference is hereby expressly made to the drawings of this patent specification. Such a nozzle consists of two parts, a base part and a top part, which are laid one above the other in order to thereby form the actual nozzle block. These two single parts can have microstructures which can be obtained e.g. by etching. Preferably the two parts are developed as plates and the microstructures form in the inside of the nozzle block a liquid connection from one side to the other, namely from the nozzle inlet side to the nozzle outlet side. There is at least one round or unround opening on the nozzle outlet side. Preferably these openings or, in the case of several, all these openings, have a depth of 2 to 10 micrometres and a width of 5 to 15 micrometres, the depth preferably being 4.5 to 6.5 micrometres and the length 7 to 9 micrometres.

In the case of several nozzle openings, two are preferred, the jet directions of the nozzles in the nozzle body can run parallel to each other or they are inclined towards each other in the direction of the nozzle opening. In the case of a nozzle body with at least two nozzle openings on the outlet side, the jet directions—and this is preferred—can be inclined towards each other, in order to atomize the liquid through the impact.

In this case the inclination angle is preferably 20 degrees to 160 degrees, preferably 60 to 150 degrees, particularly preferably 80 to 100°.

The nozzle openings are preferably arranged at a distance of 10 to 200 micrometres, more preferably at a distance of 10 to 100 micrometres, particularly preferably 30 to 70 micrometres. 50 micrometres are most strongly preferred.

The jet directions accordingly meet in the area around the nozzle openings.

The two individual parts can be worked from glass, silicon or a plastic material. Preferably the microstructures are etched into a silicon plate. Both parts have at least one essentially flat surface. When the two parts are laid one above the other, these two surfaces lie one on the other.

For the sake of simplicity a version is described in the following in which only the base part has relief-like microstructures, but not the top part. In other versions the situation is exactly the opposite or both parts have these microstructures.

A set of channels can be developed on the base part on the flat surface, in order, in cooperation with the essentially flat surface of the top part, to create a large number of filter passageways (filter channels). The base part can also have a plenum chamber, the lid of which is again formed by the top part. This plenum chamber can be located up- or downstream from the filter channels. Two such plenum chambers can also be developed. Another set of channels on the essentially flat surface of the base part, which—if present—is located downstream from the filter channels, forms together with the top part a set of channels which create a large number of nozzle outlet passageways.

The overall cross-section surface-area range of the nozzle outlets is preferably 25 to 500 square micrometres. The overall cross-section surface-area range is preferably 30 to 200 square micrometres.

In another version this nozzle structure also has only a single nozzle opening.

In other versions of this type the filter channels and/or the plenum chamber are missing.

The filter channels are preferably formed by projections which are arranged in zig-zag form. Thus for example at least two rows of the projections form such a zig-zag configuration. Several rows of projections can also be developed, the projections are in each case offset laterally relative to each other, in order to thereby build up second rows skewed to these rows, these last-described rows then forming the zig-zag configuration. In such versions the inlet and the outlet can each have a longitudinal slot for unfiltered or filtered fluid, each of the slits being essentially exactly as wide as the filter and essentially exactly as high as the projections on the inlet or outlet sides of the filter. The cross-section of the passageways formed by the projections can in each case stand perpendicular to the direction of flow of the fluids and can—seen in direction of flow—decrease from row to row. The projections which are arranged nearer to the inlet side of the filter can also be larger than the projections which are arranged nearer to the outlet side of the filter. In addition the distance between the base part and the top part can reduce in the area from the nozzle inlet side to the nozzle outlet side.

The zig-zag configuration which is formed by the at least two rows of projections has an inclination angle alpha of preferably 20° to 250°.

Further details of this nozzle structure can be found in WO-94/07607. Reference is hereby made to the contents of this document, in particular to FIG. 1 and its description.

The described nozzles can be connected to the opening of the container via a nozzle holder. Such a nozzle holder is in the simplest form a ring or body with an opening into which the nozzle can be fitted. This opening covers the nozzle block over its whole generated surface, i.e. the surface that stands perpendicular to the preferably linear axis which is formed by the nozzle inlet side and the nozzle outlet side. The holder is open to the top and bottom, in order to prevent neither the supply of liquid to the nozzle inlet side of the nozzle, nor the dispensing of the liquid. This holder can in turn be fitted into a second holder. The outer shape of the first holder is preferably conical. The opening of the second holder is formed accordingly. The first holder can consist of an elastomer.

The dispensing facility is connected in form-locking manner to the container and to this end is preferably screwed or crimped to the container via a screw cap or crimping sleeve with in each case an open side, which is particularly economical. Alternatively the form-locking connection can also be achieved by gluing or welding, in particular by means of ultrasonic welding.

In each case the connection is such that the nozzle opening lies free and cannot be blocked by the closure.

In the case of a needleless injector the nozzle is such that a sharp liquid jet is produced thereby. A funnel-shaped shield (hopper) can be developed around the nozzle, the narrowing end of which surrounds the nozzle. In this case the nozzle can be introduced via the top-side opening of the accommodation chamber into the latter. The hopper then projects from out of the top-side opening of the accommodation chamber.

During use the broad opening of the hopper is placed onto the point on the skin into which the liquid is to be injected. A spraying of the liquid is prevented by this measure.

In other versions this function can be taken over by the tubular projection of the device for the exertion of pressure if this is accordingly developed, i.e. the projection which forms a mouthpiece in the case of an inhaler.

Figure 16:
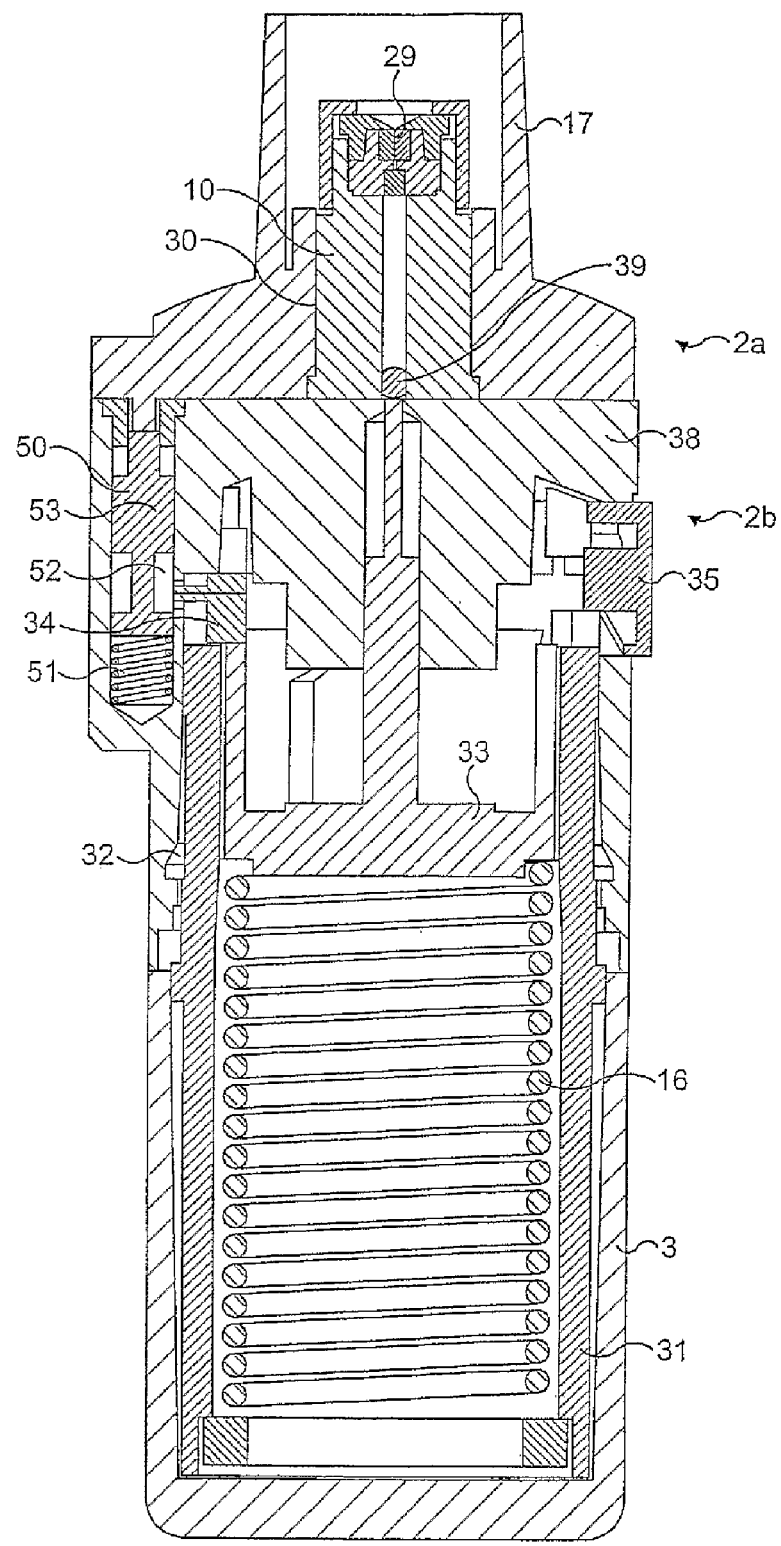
FIGS. 16 and 17 describe the device in cross-section.

FIG. 16 shows a preferred version of the device in cross-section. This representation shows the locking clamping means described by FIGS. 10 and 11 and differs only slightly from the device described there, in particular in the design of the pressure piston 6 and of the drive flange 33. Compared with the version according to FIGS. 9 and 10 the device in this version has blocking means which prevent the exertion of pressure caused by the pressing of the key 35 from being released as long as the housing upper section is open. In this version these blocking means consist of a locking bolt 50 which is housed bottom-side against a spring 51. Top-side, the locking bolt touches the bottom of the housing upper section 2a. The locking bolt has areas with larger and smaller diameters. It is situated behind the locking member 34. In the closed position of the device a recess 52 developed at the locking bolt 50 lies behind the locking member 34 and thereby frees the path for the locking member. In the opened position of the device the spring 51 of the locking bolt presses slightly upwards, so that the wider area 53 of the locking bolt 50 comes to rest behind the locking member 34 and thus blocks the release of the locking member. The release key 35 cannot be pressed in this position. In alternative versions, the spring 51 is connected top-side to the locking bolt and the mechanism is mirrored accordingly. FIG. 16 shows the closed device with tensioned compression spring 16, i.e. the top of the pressure piston 6 still lies in the housing middle section 2b.

Figure 17:
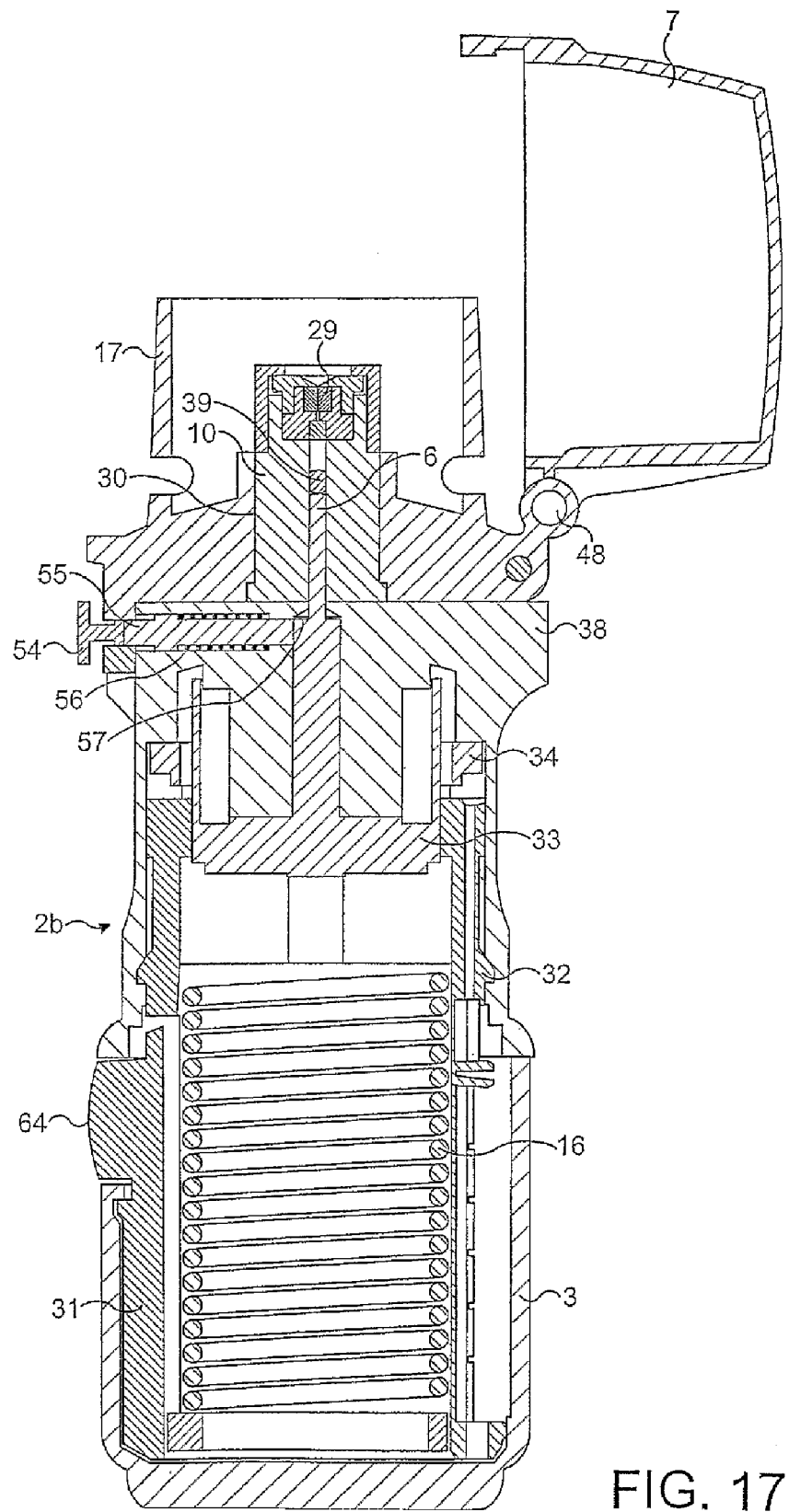

FIG. 17 shows another cross-section plane of the version according to FIG. 16 with the spring relaxed. The top of the pressure piston 6 has forced the container piston 39 into the container cartridge 10 and the liquid has been extracted from the latter through the nozzle 29. In this perspective the closure between housing lower section and compression spring housing 31 is represented under the reference number 64. The closure can be releasable or fixed, it can be achieved via a snap spring and the like. The closure arrest mechanism can also be recognized from this perspective. The closure key 54 is developed at the housing upper section 2a or at the housing middle section 2b. In the closed position of the device this touches one end of the horizontal arrester bolt 55 which is elastically housed against the spring 56. The other end of the arrester bolt lies on the pressure piston. The closure key 54 cannot be operated in this position. Only when the compression spring 16 is tensioned by rotation of the housing lower section 3 against the housing middle section 2b, the compression spring housing 31 being entrained via the closure 64 by the housing lower section, the pressure piston 6 guided back into the housing middle section, is the path for the arrester bolt released out from this position in the direction of the pressure piston. In this position the closure key 54 can be pressed and the housing upper section opened. In this version the pressure piston has a stepped constriction 57 and the freedom of movement of the arrester bolt 55 is blocked by the thicker region. In other versions the pressure piston 6 can have a constant diameter and the arrester bolt 55 is released only when the pressure piston is held by the tensioned compression spring 16 underneath the arrester bolt.

Figure 18A:
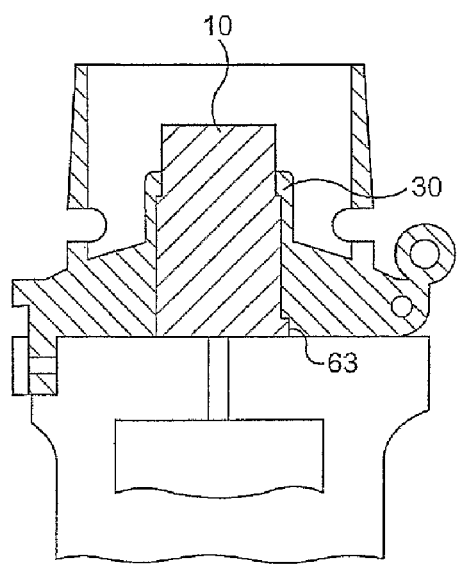
FIG. 18a to 18f show various containers with non-rotation-symmetrical outer contour elements.
Figure 18B:
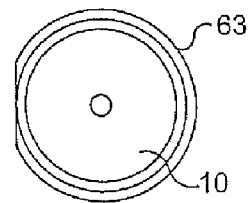

FIG. 18a shows an accommodation chamber into which a container cartridge (10) with a baseplate (63) with a cross-section in the shape of a circle segment according to FIG. 18b. is inserted. The container tapers top-side in steps. The thus-developed shoulder is held by a narrower section in the accommodation chamber.

Figure 18C:
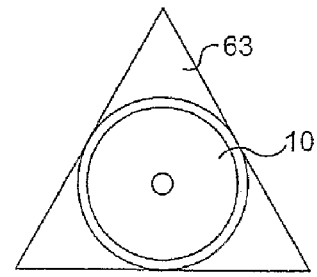
Figure 18E:
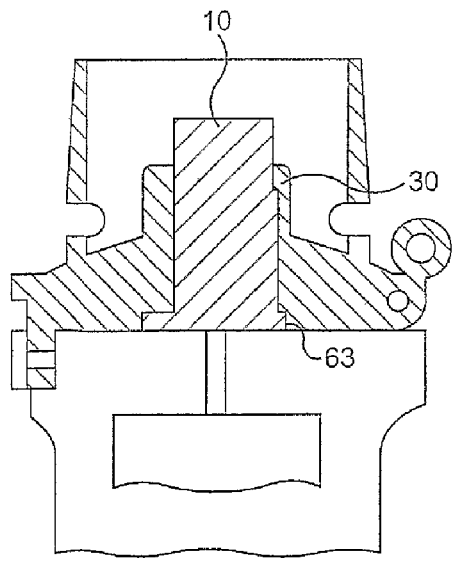
Figure 18D:
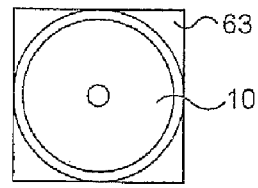

FIG. 18c shows the same container with a triangular baseplate (63) and the container according to FIG. 18d has a square baseplate (63).

Figure 18F:
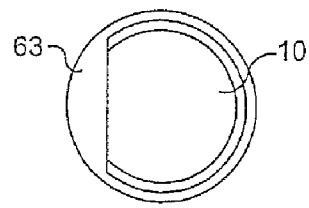

FIG. 18e shows a container (10) with a circle-segment-like cross-section but a round baseplate (63) according to FIG. 18f which is located in the accommodation chamber which is complementary thereto.

Figure 19A:
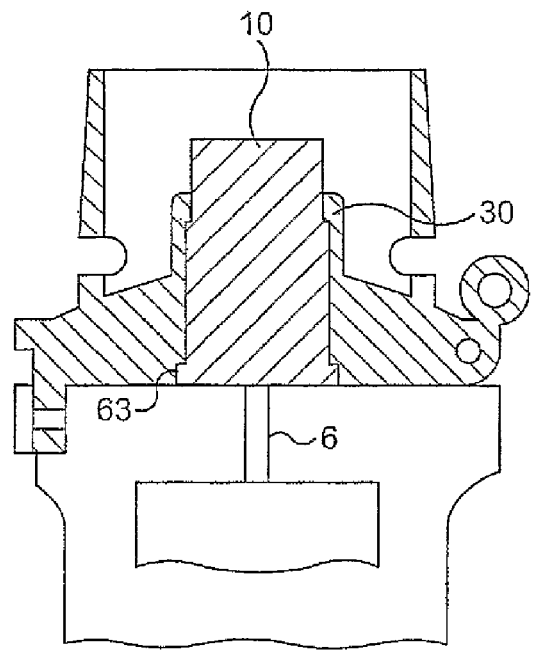
FIG. 19a and 19b show an example of an accommodation chamber for a rotation-symmetrical container in which the latter, as appropriate to its function, can be pushed into the accommodation chamber only from below.
Figure 19B:
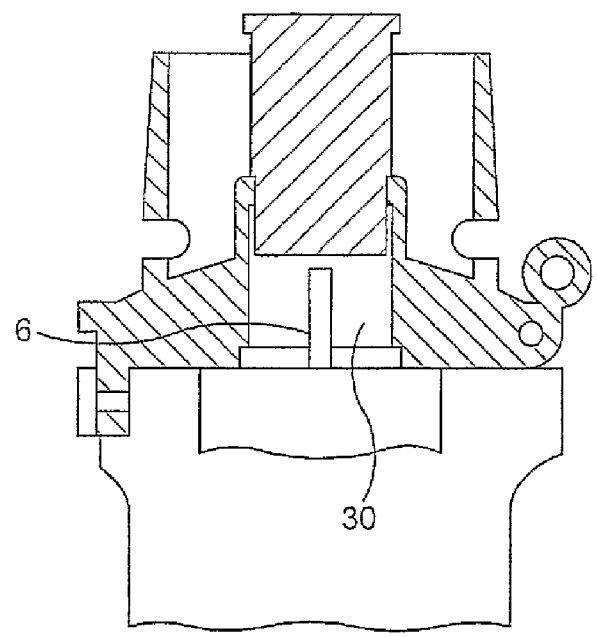

FIGS. 19a and 19b demonstrate a version which is designed such that a user of the present invention cannot injure himself if the container cartridge (10) is inadvertently introduced from above into an accommodation chamber (30) for which there is provision for the container cartridge to be fed only from below. FIG. 19a shows a container cartridge (10) which was introduced coming from below into the accommodation chamber (30). The device is in tensioned state. FIG. 19b shows the case in which the container cartridge (10) is fed from above. The device is in relaxed state. The container cartridge (10) can be pushed into the accommodation chamber (30) only by the head region, because the shoulder then strikes the top edge of the tapering accommodation chamber (30). In the relaxed state of the apparatus according to the invention, the pressure piston (6) does not extend far enough into the accommodation chamber (30) to be able to touch the container cartridge (10).

Through the device according to the invention for the exertion of pressure, a pressure is to be created in the container cartridge which presses the drug in the container with an entry pressure of up to 600 bar, 50 bar to 600 bar, particularly preferably 200 to 300 bar on the nozzle body and thus atomizes it via the nozzle openings e.g. into an inhalable aerosol. The preferred particle sizes of such an aerosol are then up to 20 micrometres, preferably 3 to 10 micrometres. In order to be able to build up this pressure, the dimensions of the pressure piston width, the length of stroke of the pressure piston, the diameter of the container piston, the capacity of the stock cylinder which now functions as pressure chamber and the force of the compression spring are chosen in accordance with the physical laws.

In addition to the advantages, described at the outset, of the invention, through the container according to the invention more highly concentrated nanosuspensions, i.e. suspensions in which the suspended particles are ca. 100-500 nm in size, can without complications be dispensed as a jet or atomized without the single use resulting practically in a blockage of the nozzles.

Via the device according to the invention, solutions or suspensions with every type of medico-therapeutically and/or medico-prophylactically effective substances are preferably dispensed. These include not only low-molecular, mostly chemico-synthetically produced, pharmacologically active substances, but also proteins, peptides, other biomacromolecules or vaccines which can be dispensed in such a device without substantial loss of activity. Reference is made to the contents of EP 1003478.

According to the invention, several replaceable reservoirs containing the fluid to be dispensed can optionally be pushed one after the other into the device for the exertion of pressure and used. The reservoir contains the corresponding pharmaceutical preparations or aerosol preparation. In such cases the device for the exertion of pressure can be fitted with a revolver magazine or a similar magazine derived from the field of rapid-fire pistols. In addition the device for the exertion of pressure can then include means which accordingly allow an automatic loading of the accommodation chamber with the reservoir cartridge.

The dispensing process is started by lightly pressing the release key. The locking means free the path for the drive part. The tensioned compression spring pushes the pressure piston into the stock cylinder of the container. The fluid emerges from the nozzle of the container—optionally in atomized form.

As already described, for an inhaler per stroke capacities of 10 to 50 microlitres are preferably atomized, capacities of 10 to 20 microlitres are particularly preferred, a capacity of 15 microlitres is quite particularly preferred.

All the components of the device for the exertion of pressure or of the container cartridge are made from a material suited to the function. The housing and—if the function allows—also other parts are preferably made from plastic material, e.g. by injection moulding. For medical purposes—if necessary—physiologically harmless materials are used.

The invention is preferably used as an atomizer of liquid drug preparations.

| LIST OF REFERENCE NUMBERS | |
|---|---|
| 1 | Device for the exertion of pressure optionally with container |
| 2 | Unit comprising housing upper section and housing middle section |
| 2a | Housing upper section |
| 2b | Housing middle section with locking clamping means |
| 3 | Housing lower section |
| 4 | Opening |
| 5 | Axis of symmetry |
| 6 | Pressure piston |
| 7 | Protective cap |
| 8a | Locking mechanism |
| 8b | Locking mechanism |
| 9 | Outlet for liquid |
| 10 | Container cartridge |
| 11 | Groove |
| 12 | Holding means |
| 13 | Movable button |
| 14 | Transport carriage |
| 15 | Clamping element/Drive flange |
| 16 | Compression spring |
| 17 | Mouthpiece |
| 18 | Grip |
| 19 | Hinge cf. 48 |
| 20 | Detent |
| 21 | Swivelling flap |
| 22 | Release button |

-continued

LIST OF REFERENCE NUMBERS

| | |
|---|---|
| 23 | Movement mechanism |
| 24 | Tongue-shaped section of the protective cap |
| 25 | Tongue-shaped recess of the housing |
| 26 | Housing |
| 27 | Hinged arm |
| 28 | Mechanical drive unit |
| 29 | Atomization facility |
| 30 | Accommodation chamber |
| 31 | Compression spring housing |
| 32 | Snap catch |
| 33 | Drive flange |
| 34 | Locking member |
| 35 | Release key cf. 46 |
| 36 | Lower stop |
| 37 | Upper stop |
| 38 | Guide cylinder |
| 39 | Container piston |
| 40 | Stock cylinder |
| 41 | Nozzle structure |
| 42 | Base part |
| 43 | Non-etched part of the base part |
| 44 | Nozzle opening |
| 45 | Filter-forming projections |
| 46 | Nozzle inlet side |
| 47 | Closure key cf. 54 |
| 48 | Hinge cf. 19 |
| 49 | Arrester bolt |
| 50 | Locking bolt |
| 51 | Spring |
| 52 | Recess |
| 53 | Thick region of the locking bolt |
| 54 | Closure key cf. 47 |
| 55 | Arrester bolt |
| 56 | Spring |
| 57 | Constriction |
| 58 | Upper sealing means |
| 59 | Lower sealing means |
| 60 | Holder |
| 61 | Crimping sleeve |
| 62 | Screw cap |
| 63 | Baseplate |
| 64 | Closure between housing lower section and compression spring housing |

The invention claimed is:

1. A device for the delivery of a drug in an aerosol of droplets by delivery of the drug under pressure, comprising:
a container cartridge having a non-pressurized cylinder therein, at rest, containing a single-dose of the drug, a piston in the cylinder, and an outlet end opposite the inlet end having a dispensing facility and means for feeding the drug thereto;
an elastic element for the storage of a predetermined quantity of energy;
a mobile element to which the predetermined quantity of energy can be fed and which is coupled to the piston such that the energy can move the piston and expose the single-dose of the drug to a predetermined increase in pressure within the cylinder; and
means for the respective introduction and removal of the container cartridge into and from an accommodation chamber within the device, wherein
the device has a housing lower section, one end of which defines a bottom-side end of the device, a housing middle section housed rotatable against the housing lower section and a housing upper section, designed at least one of vertically swivellable and eccentrically rotatable relative to the housing middle section, with the means for accommodating the container cartridge, such that an end of the housing upper section, in the closed state of the device, is not connected to the housing middle section and defines a top-side end of the device.

2. A device according to claim 1, characterized in that the container cartridge can be introduced into the accommodation chamber via an opening in a housing wall of the device.

3. A device according to claim 2, characterized in that the container cartridge, after its introduction into the housing opening, can be transferred into its end-position by a 4. A device according to claim 2, characterized in that a part of the housing wall includes a removable grip which is provided with a holding means for accommodating the container cartridge.

5. A device according to claim 1, characterized in that the container cartridge can be introduced directly into its end-position in the device.

6. A device according to claim 1, characterized in that the container cartridge can be introduced into a bore passing through the housing upper section.

7. A device according to claim 6, characterized in that there are developed on the bore one or more stops beyond which the container cannot be pushed and/or means are developed for guiding the container cartridge up to the one or more stops.

8. A device according to claim 1, characterized in that the elastic element for the storage of a predetermined quantity of energy is a helical spring which is part of a locking clamping means and via which a drive flange, which is connected to a pressure piston, is moved vertically.

9. A device according to claim 8, characterized in that the compression spring is located in a compression spring housing which is housed rotatable in the housing middle section and is connected to the housing lower section, the compression spring being tensioned via a gear system when the housing lower section and/or the compression spring housing is rotated against the housing middle section and moves a drive flange bottom-side and the compression spring remains in the tensioned position via a locking member, until a relaxation occurs due to the pressing of a release key connected to the locking member.

10. A device according to claim 9, characterized in that blocking means are developed for blocking the release key that are coupled to the closure mechanism between the housing upper section and housing lower section.

11. A device according to claim 10, characterized in that the blocking means comprise a mobile locking bolt which prevents the horizontal release movement of at least one of the locking member and the release key.

12. A device according to claim 9, characterized in that the device has closure arrest means for preventing the housing upper section from being opened as long as the compression spring is not tensioned, and the pressure piston thus projects into the housing upper section.

13. A device according to claim 12, characterized in that the closure arrest means comprise a mobile arrester bolt which prevents the release of the closure key until the pressure piston is in the position defined by the tensioned spring.

14. A system for the delivery of a predosed quantity of at least one of a medico-therapeutically effective substance and a medico-prophylactically effective substance in an aerosol of droplets by delivery of the predosed quantity of the drug under pressure by the dispensing facility, comprising a device according to claim 1.

15. A system according to claim 14, characterized in that the accommodation chamber and the container cartridge are developed to fit precisely.

16. A system according to claim 14, characterized in that it is an inhalation device.

* * * * *